United States Patent [19]
Van Baren et al.

[11] Patent Number: 5,879,892
[45] Date of Patent: Mar. 9, 1999

[54] LEUKEMIA ASSOCIATED GENES

[75] Inventors: Nicolas Van Baren; Pierre G. Coulie; Charles DeSmet; Sophie Lucas; Thierry Boon-Falleur, all of Brussels, Belgium

[73] Assignee: Ludwig Institute for Cancer Research, New York, N.Y.

[21] Appl. No.: 845,998

[22] Filed: Apr. 25, 1997

[51] Int. Cl.$^6$ .................................................... C12Q 1/68
[52] U.S. Cl. .................................................................. 435/6
[58] Field of Search ................................ 435/6; 536/24.33

[56] References Cited

U.S. PATENT DOCUMENTS

| | | | |
|---|---|---|---|
| 5,342,774 | 8/1994 | Boon et al. | 435/371 |
| 5,405,940 | 4/1995 | Boon et al. | 530/328 |
| 5,571,711 | 11/1996 | van der Bruggen et al. | 435/365 |
| 5,587,289 | 12/1996 | Lurguin | 435/6 |
| 5,589,334 | 12/1996 | Coulie et al. | 435/6 |
| 5,610,013 | 3/1997 | Van den Eynde et al. | 435/6 |
| 5,620,886 | 4/1997 | Brichard et al. | 435/325 |

FOREIGN PATENT DOCUMENTS

| | | | |
|---|---|---|---|
| PCT/US92/04354 | 5/1992 | WIPO . | |
| WO/US95/12117 | 11/1996 | WIPO . | |

OTHER PUBLICATIONS

Vanderslice et al., *Proc. Natl. Acad. Sci. USA* 87:3811–3815 (1990).
Yanada et al., *Mol. Endocrinol.* 4:551–556 (1990).
Miller et al., *J. Clin. Invest.* 84:1188–1195 (1989).
Chambost et al., *Brit. J. Haematology* 84:524–526 (1993).
Traversari et al., J. Exp. Med. 176:1453–1457 (1992).
van der Bruggen et al., Science 254:1643 (1991).
DePlaen et al., Immunogenetics 40:360–369.
Wilber, J.F., Clin. Endocr. 59:3 (1984).
Bhargava A.K. et al., Proc. Natl. Acad. Sci. USA 90:10260–10264 (1993).

*Primary Examiner*—James Ketter
*Attorney, Agent, or Firm*—Wolf, Greenfield, & Sacks, P.C.

[57] ABSTRACT

The invention describes leukemia associated genes, including fragments and biologically functional variants thereof. Also included are polypeptides and fragments thereof encoded by such genes, and antibodies relating thereto. Methods and products also are provided for diagnosing and treating conditions characterized by expression of a preproTRH, tryptase-L and/or Oct-T1 gene product.

9 Claims, 6 Drawing Sheets

SEQUENCE LISTING ( 1 ) GENERAL INFORMATION:

( i i i ) NUMBER OF SEQUENCES: 16

( 2 ) INFORMATION FOR SEQ ID NO:1:

( i ) SEQUENCE CHARACTERISTICS:
( A ) LENGTH: 1581 base pairs
( B ) TYPE: nucleic acid
( C ) STRANDEDNESS: double
( D ) TOPOLOGY: linear ( i i ) MOLECULE TYPE: cDNA ( i i i ) HYPOTHETICAL: NO ( i v ) ANTI-SENSE: NO ( i x ) FEATURE:
( A ) NAME/KEY: CDS
( B ) LOCATION: 106..831

( x i ) SEQUENCE DESCRIPTION: SEQ ID NO:1:

| | | | | | | | | | | | | | | | |
|---|---|---|---|---|---|---|---|---|---|---|---|---|---|---|---|
| CGCCCGGGGT | CCTCAGCGCT | GCAGACTCCT | GACCTGCCGA | CTGCGGATCC | CGAGTCCCCG | | | | | | | | | | 6 0 |

| | | | | | | | | | | | | | |
|---|---|---|---|---|---|---|---|---|---|---|---|---|---|
| GATCCCGGAC | CCATCCTGTG | GAGCCCACTC | CTGGCAGACG | CCGCG | ATG | CCC | GGC | | | | | | 1 1 4 |
| | | | | | Met | Pro | Gly | | | | | | |
| | | | | | 1 | | | | | | | | |

| CCT | TGG | TTG | CTG | CTC | GCT | CTG | GCT | TTG | ACC | CTG | AAC | CTG | ACC | GGT | GTC | 1 6 2 |
|---|---|---|---|---|---|---|---|---|---|---|---|---|---|---|---|---|
| Pro | Trp | Leu | Leu | Leu | Ala | Leu | Ala | Leu | Thr | Leu | Asn | Leu | Thr | Gly | Val | |
| | 5 | | | | | 1 0 | | | | | 1 5 | | | | | |

| CCC | GGC | GGC | CGT | GCT | CAG | CCA | GAG | GCG | GCC | CAG | CAG | GAG | GCA | GTG | ACG | 2 1 0 |
|---|---|---|---|---|---|---|---|---|---|---|---|---|---|---|---|---|
| Pro | Gly | Gly | Arg | Ala | Gln | Pro | Glu | Ala | Ala | Gln | Gln | Glu | Ala | Val | Thr | |
| 2 0 | | | | | 2 5 | | | | | 3 0 | | | | | 3 5 | |

| GCC | GCG | GAG | CAT | CCG | GGC | CTG | GAT | GAC | TTC | CTG | CGC | CAG | GTG | GAG | CGC | 2 5 8 |
|---|---|---|---|---|---|---|---|---|---|---|---|---|---|---|---|---|
| Ala | Ala | Glu | His | Pro | Gly | Leu | Asp | Asp | Phe | Leu | Arg | Gln | Val | Glu | Arg | |
| | | | | 4 0 | | | | | 4 5 | | | | | 5 0 | | |

```
CTC  CTC  TTC  CTC  CGG  GAA  AAC  ATC  CAG  CGG  CTG  CAA  GGG  GAC  CAG  GGT       306
Leu  Leu  Phe  Leu  Arg  Glu  Asn  Ile  Gln  Arg  Leu  Gln  Gly  Asp  Gln  Gly
               55                      60                       65

GAG  CAC  TCC  GCG  TCC  CAG  ATC  TTT  CAA  TCT  GAC  TGG  CTC  TCC  AAA  CGT       354
Glu  His  Ser  Ala  Ser  Gln  Ile  Phe  Gln  Ser  Asp  Trp  Leu  Ser  Lys  Arg
          70                           75                        80

CAG  CAT  CCA  GGC  AAA  AGA  GAG  GAG  GAG  GAG  GAA  GAG  GGA  GTT  GAA  GAA       402
Gln  His  Pro  Gly  Lys  Arg  Glu  Glu  Glu  Glu  Glu  Glu  Gly  Val  Glu  Glu
          85                           90                        95

GAG  GAA  GAG  GAA  GAA  GGG  GGG  GCT  GTG  GGA  CCC  CAC  AAA  CGG  CAG  CAC       450
Glu  Glu  Glu  Glu  Glu  Gly  Gly  Ala  Val  Gly  Pro  His  Lys  Arg  Gln  His
100                           105                      110                      115

CCT  GGC  CGA  CGA  GAA  GAT  GAG  GCT  TCA  TGG  TCA  GTC  GAT  GTA  ACC  CAG       498
Pro  Gly  Arg  Arg  Glu  Asp  Glu  Ala  Ser  Trp  Ser  Val  Asp  Val  Thr  Gln
                    120                      125                      130

CAC  AAG  CGG  CAG  CAT  CCT  GGC  CGG  CGC  TCC  CCC  TGG  CTT  GCA  TAT  GCT       546
His  Lys  Arg  Gln  His  Pro  Gly  Arg  Arg  Ser  Pro  Trp  Leu  Ala  Tyr  Ala
               135                      140                      145

GTC  CCG  AAG  CGG  CAG  CAC  CCA  GGC  AGA  AGG  CTG  GCA  GAT  CCC  AAG  GCT       594
Val  Pro  Lys  Arg  Gln  His  Pro  Gly  Arg  Arg  Leu  Ala  Asp  Pro  Lys  Ala
          150                           155                      160

CAA  AGG  AGC  TGG  GAA  GAA  GAG  GAG  GAG  GAG  GAA  GAG  AGA  GAG  GAA  GAC       642
Gln  Arg  Ser  Trp  Glu  Glu  Glu  Glu  Glu  Glu  Glu  Glu  Arg  Glu  Glu  Asp
165                           170                      175

CTG  ATG  CCT  GAA  AAA  CGC  CAG  CAT  CCG  GGC  AAG  AGG  GCC  CTG  GGA  GGC       690
Leu  Met  Pro  Glu  Lys  Arg  Gln  His  Pro  Gly  Lys  Arg  Ala  Leu  Gly  Gly
180                           185                      190                      195

CCC  TGT  GGG  CCC  CAG  GGA  GCC  TAT  GGT  CAA  GCG  GGC  CTC  CTG  CTG  GGG       738
Pro  Cys  Gly  Pro  Gln  Gly  Ala  Tyr  Gly  Gln  Ala  Gly  Leu  Leu  Leu  Gly
                    200                      205                      210

CTC  CTG  GAT  GAC  CTG  AGT  AGG  AGC  CAG  GGA  GCT  GAG  GAA  AAG  CGG  CAG       786
Leu  Leu  Asp  Asp  Leu  Ser  Arg  Ser  Gln  Gly  Ala  Glu  Glu  Lys  Arg  Gln
               215                      220                      225

CAC  CCT  GGT  CGG  CGG  GCA  GCC  TGG  GTC  AGG  GAG  CCC  CTG  GAG  GAG            831
His  Pro  Gly  Arg  Arg  Ala  Ala  Trp  Val  Arg  Glu  Pro  Leu  Glu  Glu
          230                           235                      240

TGAACCCAGT  TTTCCCTGAA  GTCGAGTTTG  TGGTCTAAGG  ATGTCTTGAG  CCCTGTGTGC       891
CCCACCATTC  ATGACCTCTG  TATTCTCTAG  TTAGATCCCT  GACCATAAGC  CTGAGCCCCT       951
CCCTCCCAGC  CCCATATTCA  CACACATCCC  AGCCCTGGC   CTTGCCCTCT  TCCTTTAGGC      1011
ATGTGAGAAA  ATCAGCCTAG  CAGTTTAAAC  CCCACTTTCC  TCCACTTAGC  ACCATAGGCA      1071
AGGGGGCAGA  TCCCAGAGCC  CCTCTCACCC  CCCCACCAC   AGGCCTGCTC  CTTCCTTAGC      1131
CTTGGCTAAG  ATGGTCCTTC  TGTGTCTTGC  AAAGACTCCC  CAAGTGGGAC  AGGGAGCCCC      1191
TGGGAGGGCA  GCCAGTGAGG  GTGGGGTGGG  ACTGAAGCGT  TGTGTGCAAA  TCCAGCTTCC      1251
ATCCCTCCC   CAACCTGGCA  GGATTCTCCA  TGTGTAAACT  TCACCCCCAG  GACCCAGGAT      1311
CTTCTCCTTT  CTGGGCATCC  CTTTGTGGGT  GGGCAGAGCC  CTGACCCACA  GCTGTGTTAC      1371
TGCTTGGAGA  AGCATATGTA  GGGGCATACC  CTGTGGTGTT  GTGCTGTGTC  TGGCTGTGGG      1431
ATAAATGTGT  GTGGGAATAT  TGAAACATCG  CCTAGGAATT  GTGGTTTGTA  TATAACCCTC      1491
TAAGCCCCTA  TCCCTTGTCG  ATGACAGTCA  TCCTAATGAT  AATAAAACCT  GCATCCAGAT      1551
AAAAAAAAAA  AAAAAAAAAA  AAAAAAAAA                                          1581
```

( 2 ) INFORMATION FOR SEQ ID NO:2:

( i ) SEQUENCE CHARACTERISTICS:
        ( A ) LENGTH: 242 amino acids ( B ) TYPE: amino acid
( D ) TOPOLOGY: linear ( i i ) MOLECULE TYPE: protein ( x i ) SEQUENCE DESCRIPTION: SEQ ID NO:2:

```
Met Pro Gly Pro Trp Leu Leu Leu Ala Leu Ala Leu Thr Leu Asn Leu
 1               5                  10                  15

Thr Gly Val Pro Gly Gly Arg Ala Gln Pro Glu Ala Ala Gln Gln Glu
            20                  25                  30

Ala Val Thr Ala Ala Glu His Pro Gly Leu Asp Asp Phe Leu Arg Gln
            35                  40                  45

Val Glu Arg Leu Leu Phe Leu Arg Glu Asn Ile Gln Arg Leu Gln Gly
    50                  55                  60

Asp Gln Gly Glu His Ser Ala Ser Gln Ile Phe Gln Ser Asp Trp Leu
65                  70                  75                  80

Ser Lys Arg Gln His Pro Gly Lys Arg Glu Glu Glu Glu Glu Glu Gly
                85                  90                  95

Val Glu Glu Glu Glu Glu Glu Glu Gly Gly Ala Val Gly Pro His Lys
                100                 105                 110

Arg Gln His Pro Gly Arg Arg Glu Asp Glu Ala Ser Trp Ser Val Asp
            115                 120                 125

Val Thr Gln His Lys Arg Gln His Pro Gly Arg Arg Ser Pro Trp Leu
    130                 135                 140

Ala Tyr Ala Val Pro Lys Arg Gln His Pro Gly Arg Arg Leu Ala Asp
145                 150                 155                 160

Pro Lys Ala Gln Arg Ser Trp Glu Glu Glu Glu Glu Glu Glu Glu Arg
                165                 170                 175

Glu Glu Asp Leu Met Pro Glu Lys Arg Gln His Pro Gly Lys Arg Ala
            180                 185                 190

Leu Gly Gly Pro Cys Gly Pro Gln Gly Ala Tyr Gly Gln Ala Gly Leu
        195                 200                 205

Leu Leu Gly Leu Leu Asp Asp Leu Ser Arg Ser Gln Gly Ala Glu Glu
    210                 215                 220

Lys Arg Gln His Pro Gly Arg Arg Ala Ala Trp Val Arg Glu Pro Leu
225                 230                 235                 240

Glu Glu
```

( 2 ) INFORMATION FOR SEQ ID NO:3:

( i ) SEQUENCE CHARACTERISTICS:
( A ) LENGTH: 2259 base pairs
( B ) TYPE: nucleic acid
( C ) STRANDEDNESS: double
( D ) TOPOLOGY: linear ( i i ) MOLECULE TYPE: cDNA ( i i i ) HYPOTHETICAL: NO ( i v ) ANTI-SENSE: NO ( i x ) FEATURE:
( A ) NAME/KEY: CDS
( B ) LOCATION: 8..577

( x i ) SEQUENCE DESCRIPTION: SEQ ID NO:3:

```
GGCCAGG ATG CTG AGC CTG CTG CTG CTG GCG CTG CCC GTC CTG GCG AGC      49
        Met Leu Ser Leu Leu Leu Leu Ala Leu Pro Val Leu Ala Ser
         1               5                  10

CCG GCC TAC GTG GCC CCT GCC CCA GGC CAG GCC CTG CAG CAA ACG GGC      97
```

| | | | | | | | | | | | | | | | |
|---|---|---|---|---|---|---|---|---|---|---|---|---|---|---|---|
|Pro|Ala|Tyr|Val|Ala|Pro|Ala|Pro|Gly|Gln|Ala|Leu|Gln|Gln|Thr|Gly|
|15| | | |20| | | |  |25| | | | |30| |

| ATT | GTT | GGG | GGG | CAG | GAG | GCC | CCC | AGG | AGC | AAG | TGG | CCC | TGG | CAG | GTG | 145 |
|---|---|---|---|---|---|---|---|---|---|---|---|---|---|---|---|---|
| Ile | Val | Gly | Gly | Gln | Glu | Ala | Pro | Arg | Ser | Lys | Trp | Pro | Trp | Gln | Val | |
| | | | | 35 | | | | 40 | | | | | 45 | | | |

| AGC | CTG | AGA | GTC | CGC | GGC | CCA | TAC | TGG | ATG | CAC | TTC | TGC | GGG | GGC | TCC | 193 |
|---|---|---|---|---|---|---|---|---|---|---|---|---|---|---|---|---|
| Ser | Leu | Arg | Val | Arg | Gly | Pro | Tyr | Trp | Met | His | Phe | Cys | Gly | Gly | Ser | |
| | | | 50 | | | | 55 | | | | | 60 | | | | |

| CTC | ATC | CAC | CCC | CAG | TGG | GTG | CTA | ACC | GCG | GCG | CAC | TGC | GTG | GAA | CCG | 241 |
|---|---|---|---|---|---|---|---|---|---|---|---|---|---|---|---|---|
| Leu | Ile | His | Pro | Gln | Trp | Val | Leu | Thr | Ala | Ala | His | Cys | Val | Glu | Pro | |
| | | 65 | | | | 70 | | | | 75 | | | | | | |

| GAC | ATC | AAG | GAT | CTG | GCC | GCC | CTC | AGG | GTG | CAA | CTG | CGG | GAG | CAG | CAC | 289 |
|---|---|---|---|---|---|---|---|---|---|---|---|---|---|---|---|---|
| Asp | Ile | Lys | Asp | Leu | Ala | Ala | Leu | Arg | Val | Gln | Leu | Arg | Glu | Gln | His | |
| | 80 | | | | 85 | | | | 90 | | | | | | | |

| CTC | TAC | TAC | CAG | GAC | CAG | CTG | CTG | CCG | GTC | AGC | AGG | ATC | ATC | GTG | CAC | 337 |
|---|---|---|---|---|---|---|---|---|---|---|---|---|---|---|---|---|
| Leu | Tyr | Tyr | Gln | Asp | Gln | Leu | Leu | Pro | Val | Ser | Arg | Ile | Ile | Val | His | |
| 95 | | | | 100 | | | | | 105 | | | | | 110 | | |

| CCA | CAG | TTC | TAC | ATC | ATC | CAG | ACC | GGG | GCG | GAC | ATC | GCC | CTG | CTG | GAG | 385 |
|---|---|---|---|---|---|---|---|---|---|---|---|---|---|---|---|---|
| Pro | Gln | Phe | Tyr | Ile | Ile | Gln | Thr | Gly | Ala | Asp | Ile | Ala | Leu | Leu | Glu | |
| | | | | 115 | | | | 120 | | | | | 125 | | | |

| CTG | GAG | GAG | CCC | GTG | AAC | ATC | TCC | AGC | CAC | ATC | CAC | ACG | GTC | ACG | CTG | 433 |
|---|---|---|---|---|---|---|---|---|---|---|---|---|---|---|---|---|
| Leu | Glu | Glu | Pro | Val | Asn | Ile | Ser | Ser | His | Ile | His | Thr | Val | Thr | Leu | |
| | | | 130 | | | | 135 | | | | | 140 | | | | |

| CCC | CCT | GCC | TCG | GAG | ACC | TTC | CCC | CCG | GGG | ATG | CCG | TGC | TGG | GTC | ACT | 481 |
|---|---|---|---|---|---|---|---|---|---|---|---|---|---|---|---|---|
| Pro | Pro | Ala | Ser | Glu | Thr | Phe | Pro | Pro | Gly | Met | Pro | Cys | Trp | Val | Thr | |
| | | 145 | | | | 150 | | | | 155 | | | | | | |

| GGC | TGG | GGC | GAC | GTG | GAC | AAT | AAT | GGT | GGG | TGT | TGG | GGA | CAG | CGG | GAG | 529 |
|---|---|---|---|---|---|---|---|---|---|---|---|---|---|---|---|---|
| Gly | Trp | Gly | Asp | Val | Asp | Asn | Asn | Gly | Gly | Cys | Trp | Gly | Gln | Arg | Glu | |
| | 160 | | | | 165 | | | | 170 | | | | | | | |

| GCC | GGG | CCA | GGT | GGG | CAC | CAA | GTC | ACA | GCC | ACA | GGC | CAG | TCC | GTG | GGG | 577 |
|---|---|---|---|---|---|---|---|---|---|---|---|---|---|---|---|---|
| Ala | Gly | Pro | Gly | Gly | His | Gln | Val | Thr | Ala | Thr | Gly | Gln | Ser | Val | Gly | |
| 175 | | | | 180 | | | | | 185 | | | | | 190 | | |

| TGACAGGGTC | CCTCAGGGCG | GCTCAGGGAG | GGGGACTGTG | GAGGCCAGGA | TGGATGGAGC | 637 |
|---|---|---|---|---|---|---|
| AGGCGGTGGC | GAGAGGCAGC | AGGTGCCCTG | AGCAGAGACG | GTGAGTCCAA | AGGGCCTGGG | 697 |
| CGTCCCCCAC | CCCAGGGGTT | TGGAGAGTCC | CTTAGCACCT | CCGTGCCTCG | GTTTCCCCTT | 757 |
| GCCTGAAAGG | GTGCATCAAA | AGTTTGTACG | TCACGGACTT | GCTATGTGGA | GAGAGAAATC | 817 |
| ACACGGGGGT | CTTGCTGGAA | GGAGAGAGAC | CGGTGCTGGG | ATGAGACCTG | CCTGCCCTCC | 877 |
| ATCCCTGTGC | TACAGACAAG | GCAGGGGCCT | GGGAATCGGG | GTCGTGGCAG | TGCTGTGGGG | 937 |
| GGCTGGACGA | AGCTCACTGT | GGCCCTCCAC | GAGGCACATT | TTCACTTCTA | GAAGGTCTTG | 997 |
| TCCCCATTTT | ATCCACAATT | CAGAGCAAAG | CTTTGGGGTA | CAGCCTGACG | CAACCCTGGG | 1057 |
| CTGTGACCTC | TGGGTCACTC | CAGAAGGGGC | CTGAGCCACT | GTCCCGCTAT | CCGCCCCAC | 1117 |
| ACAGCGGGGA | AGCTGAGCCC | AGCGCCCTGT | GTTCCCCTCG | GCTAGGGCCA | ACCGTGGACC | 1177 |
| ATGGGCCTAG | CCCAGACGAA | AGTCAGCTGA | GCCAGGGGG | AGACACGGGT | CGGGCTCTGC | 1237 |
| ACCCCCGTGC | CATGGAGCCC | AGCTTGGCAA | CCTCCAGGGC | CCTCCCCTCC | CTTCCCCAGA | 1297 |
| TGGGGCTTAA | ATGAGGCCAG | GGACCCAGGA | CCAGCCTCAG | CGGAGGGGCC | TGGACTGCAT | 1357 |
| TCACCGCCCC | TTCCCCGGGG | CTGCAGGCAC | AGAACAGCAC | TGGGCCCATG | GTGCCATCTC | 1417 |
| CCCTGCCCGT | GACTCTGCCA | CCAAGTCCAC | GAAGCAGCAC | CCAGCCGGCC | CCAGACCCGG | 1477 |
| CTCCACGCCC | CCCTCCGCCC | CCAGTGCACC | TGCCGCCGCC | ATACCGCTG | AAGGAGGTGG | 1537 |
| AAGTCCCCGT | AGTGGAAAAC | CACCTTTGCA | ACGCGGAATA | TCACACCGGC | CTCCATACGG | 1597 |
| GCCACAGCTT | TCAAATCGTC | CGCGATGACA | TGCTGTGTGC | GGGGAGCGAA | AATCACGACT | 1657 |
| CCTGCCAGGG | TGACTCTGGA | GGGCCCCTGG | TCTGCAAGGT | GAATGGCACC | TAACTGCAGG | 1717 |

| | | | | | |
|---|---|---|---|---|---|
| CGGCCGTGGT | CAGCTGGGAG | GAGAGCTGTG | CCCAGCCCAA | CCGGCCTGGC | ATCTACACCC | 1777 |
| GTGTCACCTA | CTACTTGGAC | TGGATCCACC | ACTATGTCCC | CAAGAAGCCC | TGACCCAGGC | 1837 |
| CTGGGTTGTC | CACCCGGGTC | ACTGGAGGGC | CAGCCCCTCC | TGTCCAAACC | ACCACTGCTT | 1897 |
| CCTACCCAGG | TGGTGACTAA | ACCCCACACC | TTCCCCCATC | CTGAGTCCCC | TCTCCCATCC | 1957 |
| TGAGCCCTGT | CCCTGTCCT  | GAGCCCCTC  | CCCTTTCTTG | ATCCCTCCC  | CCATCCTGAG | 2017 |
| CCCCCTCCCC | CACCCTGAGC | CCCCTCCCCT | GTCTTGAGCC | CCTCATCCAT | CCTGAGCCCC | 2077 |
| TCCTCCATCC | TGAGCCCCCT | CCCCCATCCT | GGGCCCCCTC | CCCTTTCTTG | AGCCCCCTCC | 2137 |
| CCCACCCTGA | GCCCCTTCCC | CTTTCTTGAG | CCCCTCCTCC | ACCCTCAGCC | CCCTCCCCTT | 2197 |
| TCTTGAGCCC | CTCCTCCACC | CTCAGCCCCC | TCCCCTTTCT | TGAGCCCCTC | CCCCACCCTG | 2257 |
| AG | | | | | | 2259 |

( 2 ) INFORMATION FOR SEQ ID NO:4:

( i ) SEQUENCE CHARACTERISTICS:
        ( A ) LENGTH: 190 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

```
Met Leu Ser Leu Leu Leu Leu Ala Leu Pro Val Leu Ala Ser Pro Ala
 1               5                  10                 15

Tyr Val Ala Pro Ala Pro Gly Gln Ala Leu Gln Gln Thr Gly Ile Val
                20              25                 30

Gly Gly Gln Glu Ala Pro Arg Ser Lys Trp Pro Trp Gln Val Ser Leu
            35              40                 45

Arg Val Arg Gly Pro Tyr Trp Met His Phe Cys Gly Gly Ser Leu Ile
        50              55              60

His Pro Gln Trp Val Leu Thr Ala Ala His Cys Val Glu Pro Asp Ile
 65                  70                 75                  80

Lys Asp Leu Ala Ala Leu Arg Val Gln Leu Arg Glu Gln His Leu Tyr
                85                  90                 95

Tyr Gln Asp Gln Leu Leu Pro Val Ser Arg Ile Ile Val His Pro Gln
                100                 105                110

Phe Tyr Ile Ile Gln Thr Gly Ala Asp Ile Ala Leu Leu Glu Leu Glu
            115                 120                125

Glu Pro Val Asn Ile Ser Ser His Ile His Thr Val Thr Leu Pro Pro
    130                 135                 140

Ala Ser Glu Thr Phe Pro Pro Gly Met Pro Cys Trp Val Thr Gly Trp
145                 150                 155                 160

Gly Asp Val Asp Asn Asn Gly Gly Cys Trp Gly Gln Arg Glu Ala Gly
                165                 170                 175

Pro Gly Gly His Gln Val Thr Ala Thr Gly Gln Ser Val Gly
                180                 185                 190
```

( 2 ) INFORMATION FOR SEQ ID NO:5:

( i ) SEQUENCE CHARACTERISTICS:
        ( A ) LENGTH: 2218 base pairs
        ( B ) TYPE: nucleic acid
        ( C ) STRANDEDNESS: double
        ( D ) TOPOLOGY: linear ( i i ) MOLECULE TYPE: cDNA ( i i i ) HYPOTHETICAL: NO ( i v ) ANTI-SENSE: NO ( v i i ) IMMEDIATE SOURCE:
  ( B ) CLONE: NVB352/3

( i x ) FEATURE:
  ( A ) NAME/KEY: CDS
  ( B ) LOCATION: 8..577

( x i ) SEQUENCE DESCRIPTION: SEQ ID NO:5:

```
GGCCAGG ATG CTG AGC CTG CTG CTG CTG GCG CTG CCC GTC CTG GCG AGC        49
        Met Leu Ser Leu Leu Leu Leu Ala Leu Pro Val Leu Ala Ser
        1               5                   10

CCG GCC TAC GTG GCC CCT GCC CCA GGC CAG GCC CTG CAG CAA ACG GGC        97
Pro Ala Tyr Val Ala Pro Ala Pro Gly Gln Ala Leu Gln Gln Thr Gly
15              20                  25                  30

ATT GTT GGG GGG CAG GAG GCC CCC AGG AGC AAG TGG CCC TGG CAG GTG       145
Ile Val Gly Gly Gln Glu Ala Pro Arg Ser Lys Trp Pro Trp Gln Val
                35                  40                  45

AGC CTG AGA GTC CGC GGC CCA TAC TGG ATG CAC TTC TGC GGG GGC TCC       193
Ser Leu Arg Val Arg Gly Pro Tyr Trp Met His Phe Cys Gly Gly Ser
        50                  55                  60

TTC ATC CAC CCC CAG TGG GTG CTA ACC GCG GCG CAC TGC GTG GAA CCG       241
Phe Ile His Pro Gln Trp Val Leu Thr Ala Ala His Cys Val Glu Pro
        65                  70                  75

GAC ATC AAG GAT CTG GCC GCC CTC AGG GTG CAA CTG CGG GAG CAG CAC       289
Asp Ile Lys Asp Leu Ala Ala Leu Arg Val Gln Leu Arg Glu Gln His
        80                  85                  90

CTC TAC TAC CAG GAC CAG CTG CTG CCG GTC AGC AGG ATC ATC GTG CAC       337
Leu Tyr Tyr Gln Asp Gln Leu Leu Pro Val Ser Arg Ile Ile Val His
95                  100                 105                 110

CCA CAG TTC TAC ATC ATC CAG ACC GGG GCG GAC ATC GCC CTG CTG GAG       385
Pro Gln Phe Tyr Ile Ile Gln Thr Gly Ala Asp Ile Ala Leu Leu Glu
                115                 120                 125

CTG GAG GAG CCC GTG AAC ATC TCC AGC CAC ATC CAC ACG GTC ACG CTG       433
Leu Glu Glu Pro Val Asn Ile Ser Ser His Ile His Thr Val Thr Leu
                130                 135                 140

CCC CCT GCC TCG GAG ACC TTC CCC CCG GGG ATG CCG TGC TGG GTC ACT       481
Pro Pro Ala Ser Glu Thr Phe Pro Pro Gly Met Pro Cys Trp Val Thr
        145                 150                 155

GGC TGG GGC GAC GTG GAC AAT AAT GGT GGG TGT TGG GGA CAG CGG GAG       529
Gly Trp Gly Asp Val Asp Asn Asn Gly Gly Cys Trp Gly Gln Arg Glu
        160                 165                 170

GCC GGG CCA GGT GGG CAC CAA GTC ACA GCC ACA GGC CAG TCC GTG GGG       577
Ala Gly Pro Gly Gly His Gln Val Thr Ala Thr Gly Gln Ser Val Gly
175             180                 185                 190

TGACAGGGTC CCTCAGGGCG GCTCAGGGAG GGGGACTGTG GAGGCCAGGA TGGATGGAGC     637

AGGCGGTGGC GAGAGGCAGC AGGTGCCCTG AGCAGAGACG GTGAGTCCAA AGGGCCTGGG     697

CGTCCCCCAC CCCAGGGGTT TGGAGAGTCC CTTAGCACCT CCGTGCCTCG GTTTCCCCTT     757

GCCTGAAAGG GTGCATCAAA AGTTTGTACG TCACGGACTT GCTATGTGGA GAGAGAAATC     817

ACACGGGGGT CTTGCTGGAA GGAGAGAGAT CGGTGCTGGG ATGAGACCTG CCTGCCCTCC     877

ATCCCTGTGC TACAGACAAG GCAGGGGCCT GGGAATCGGG GTCGTGGCAG TGCTGTGGGG     937

GGCTGGACGA AGCTCACTGT GGCCCTCCAC GAGGCACATT TTCACTTCTA GAAGGTCTTG     997

TCCCCATTTT ATCCACAATT CAGAGCAAAG CTTTGGGGTA CAGCCTGAGC GGCAACCCTG    1057

GGCTGTGACT CTGGGTCACT CAGAAGGGGC CTGAGCCACT GTCCCGCTAT TCCGCCCCAC    1117

ACAGCGGGGA AGCTGAGCCC AGCGCCCTGT GTTCCCCTCG GCTAGGGCCA ACCGTGGACC    1177
```

```
ATGGGCCTAG CCCAGACGAA AGTCAGCTGA GCCCAGGGGG AGACACGGGT CGGGCTCTGC    1237
ACCCCCGTGC CATGGAGCCC AGCTTGGCAA CCTCCAGGGC CCTCCCCTCC CTTCCCCAGA    1297
TGGGGCTTAA ATGAGGCCAG GGACCCAGGA CCAGCCTCAG CGGAGGGGCC TGGACTGCAT    1357
TCACCGCCCC TTCCCCGGGG CTGCAGGCAC AGAACAGCAC TGGGCCCATG GTGCCATCTC    1417
CCCTGCCCGT GACTCTGCCA CCAAGTCCAC GAAGCAGCAC CCAGCCGGCC CCAGACCCGG    1477
CTCCACGCCC CCCTCCGCCC CCAGTGCACC TGCCGCCGCC ATACCCGCTG AAGGAGGTGG    1537
AAGTCCCCGT AGTGGAAAAC CACCTTTGCA ACGCGGAATA TCACACCGGC CTCCATACGG    1597
GCCACAGCTT TCAAATCGTC CGCGATGACA TGCTGTGTGC GGGGAGCGAA AATCACGACT    1657
CCTGCCAGGT GGGCCCTCGC GTCCCCCACC CCAATCCCCG GAGCCTGGCC AGCGAGCGCA    1717
TCCCTCATCC TGACCCCCGA AGCCTGGCCA GCGAGCACTG ACCTCTGACC TTCCCAGGGT    1777
GACTCTGGAG GGCCCCTGGT CTGCAAGGTG AATGGCACCT AACTGCAGGC GGGCGTGGTC    1837
AGCTGGGAGG AGAGCTGTGC CCAGCCCAAC CGGCCTGGCA TCTACACCCG TGTCACCTAC    1897
TACTTGGACT GGATCCACCA CTATGTCCCC AAGAAGCCCT GAGCCAGGCC TGGGGTGTCC    1957
ACCCGGGTCA CTGGAGGGCC AGCCCTCCT GTCCAAACCA CCACTGCTTC CTACCCAGGT    2017
GGTGACTGCC CCCCACACCT TCCCCCATCC TGAGTCCCCT CTCCCATCCT GAGCCCTGTC    2077
CCCTGTCCTG AGCCCCCTCC CCTTTCTTGA TCCCCTCCCC CATCCTGAGC CCCCTCCCCC    2137
ACCCTGAGCC CCCTCCCCTG TCTTGAGCCC CTGCTCCATC CTGAGTCCCC TCCCCCACAC    2197
TGAGCCCCCT CCCCTTTCTT G                                              2218
```

( 2 ) INFORMATION FOR SEQ ID NO:6:

( i ) SEQUENCE CHARACTERISTICS:
        ( A ) LENGTH: 190 amino acids
        ( B ) TYPE: amino acid
        ( D ) TOPOLOGY: linear ( i i ) MOLECULE TYPE: protein ( x i ) SEQUENCE DESCRIPTION: SEQ ID NO:6:

```
Met Leu Ser Leu Leu Leu Ala Leu Pro Val Leu Ala Ser Pro Ala
 1               5                  10                  15

Tyr Val Ala Pro Ala Pro Gly Gln Ala Leu Gln Gln Thr Gly Ile Val
                20                  25                  30

Gly Gly Gln Glu Ala Pro Arg Ser Lys Trp Pro Trp Gln Val Ser Leu
            35                  40                  45

Arg Val Arg Gly Pro Tyr Trp Met His Phe Cys Gly Gly Ser Phe Ile
        50                  55                  60

His Pro Gln Trp Val Leu Thr Ala Ala His Cys Val Glu Pro Asp Ile
65                  70                  75                  80

Lys Asp Leu Ala Ala Leu Arg Val Gln Leu Arg Glu Gln His Leu Tyr
                85                  90                  95

Tyr Gln Asp Gln Leu Leu Pro Val Ser Arg Ile Ile Val His Pro Gln
               100                 105                 110

Phe Tyr Ile Ile Gln Thr Gly Ala Asp Ile Ala Leu Leu Glu Leu Glu
           115                 120                 125

Glu Pro Val Asn Ile Ser Ser His Ile His Thr Val Thr Leu Pro Pro
       130                 135                 140

Ala Ser Glu Thr Phe Pro Pro Gly Met Pro Cys Trp Val Thr Gly Trp
145                 150                 155                 160

Gly Asp Val Asp Asn Asn Gly Gly Cys Trp Gly Gln Arg Glu Ala Gly
```

|  |  | 165 |  |  |  |  | 170 |  |  |  |  | 175 |  |
|---|---|---|---|---|---|---|---|---|---|---|---|---|---|
| Pro | Gly | Gly | His | Gln | Val | Thr | Ala | Thr | Gly | Gln | Ser | Val | Gly |
|  |  |  | 180 |  |  |  |  | 185 |  |  |  |  | 190 |

( 2 ) INFORMATION FOR SEQ ID NO:7:

( i ) SEQUENCE CHARACTERISTICS:
        ( A ) LENGTH: 4524 base pairs
        ( B ) TYPE: nucleic acid
        ( C ) STRANDEDNESS: double
        ( D ) TOPOLOGY: linear ( i i ) MOLECULE TYPE: cDNA ( i i i ) HYPOTHETICAL: NO ( i v ) ANTI-SENSE: NO ( i x ) FEATURE:
        ( A ) NAME/KEY: CDS
        ( B ) LOCATION: 174..1433

( x i ) SEQUENCE DESCRIPTION: SEQ ID NO:7:

| CAGAGGGAGC | GCCTGGCAGC | AGCAGGAGCA | GCAGCAGCAG | CCCGCGGCGG | GGCCGCCGCC | 60 |
|---|---|---|---|---|---|---|
| AGCCGCCGCG | ACCGCCGCGG | CTGCAGCCTC | CGAAGGGAGG | CCGGGTGAGC | CGGCGTACGC | 120 |
| ACTTTCCCGC | GGACTTTCGG | AGTGTTTGTG | GATATACATG | CCAAGCCGCC | ACG ATG | 176 |
|  |  |  |  |  | Met |  |
|  |  |  |  |  | 1 |  |

| ATG | TCC | ATG | AAC | AGC | AAG | CAG | CCT | CAC | TTT | GCC | ATG | CAT | CCC | ACC | CTC | 224 |
|---|---|---|---|---|---|---|---|---|---|---|---|---|---|---|---|---|
| Met | Ser | Met | Asn | Ser | Lys | Gln | Pro | His | Phe | Ala | Met | His | Pro | Thr | Leu |  |
|  |  |  |  | 5 |  |  |  | 10 |  |  |  |  | 15 |  |  |  |

| CCT | GAG | CAC | AAG | TAC | CCG | TCG | CTG | CAC | TCC | AGC | TCC | GAG | GCC | ATC | CGG | 272 |
|---|---|---|---|---|---|---|---|---|---|---|---|---|---|---|---|---|
| Pro | Glu | His | Lys | Tyr | Pro | Ser | Leu | His | Ser | Ser | Ser | Glu | Ala | Ile | Arg |  |
|  |  | 20 |  |  |  |  | 25 |  |  |  |  | 30 |  |  |  |  |

| CGG | GCC | TGC | CTG | CCC | ACG | CCG | CCG | CTG | CAG | AGC | AAC | CTC | TTC | GCC | AGC | 320 |
|---|---|---|---|---|---|---|---|---|---|---|---|---|---|---|---|---|
| Arg | Ala | Cys | Leu | Pro | Thr | Pro | Pro | Leu | Gln | Ser | Asn | Leu | Phe | Ala | Ser |  |
|  |  | 35 |  |  |  | 40 |  |  |  |  | 45 |  |  |  |  |  |

| CTG | GAC | GAG | ACG | CTG | CTG | GCG | CGG | GCC | GAG | GCG | CTG | GCG | GCC | GTG | GAC | 368 |
|---|---|---|---|---|---|---|---|---|---|---|---|---|---|---|---|---|
| Leu | Asp | Glu | Thr | Leu | Leu | Ala | Arg | Ala | Glu | Ala | Leu | Ala | Ala | Val | Asp |  |
| 50 |  |  |  |  | 55 |  |  |  |  | 60 |  |  |  |  | 65 |  |

| ATC | GCC | GTG | TCC | CAG | GGC | AAG | AGC | CAT | CCT | TTC | AAG | CCG | GAC | GCC | ACG | 416 |
|---|---|---|---|---|---|---|---|---|---|---|---|---|---|---|---|---|
| Ile | Ala | Val | Ser | Gln | Gly | Lys | Ser | His | Pro | Phe | Lys | Pro | Asp | Ala | Thr |  |
|  |  |  |  | 70 |  |  |  |  | 75 |  |  |  |  | 80 |  |  |

| TAC | CAC | ACG | ATG | AAC | AGC | GTG | CCG | TGC | ACG | TCC | ACT | TCC | ACG | GTG | CCT | 464 |
|---|---|---|---|---|---|---|---|---|---|---|---|---|---|---|---|---|
| Tyr | His | Thr | Met | Asn | Ser | Val | Pro | Cys | Thr | Ser | Thr | Ser | Thr | Val | Pro |  |
|  |  |  | 85 |  |  |  |  | 90 |  |  |  |  | 95 |  |  |  |

| CTG | GCG | CAC | CAC | CAC | CAC | CAC | CAC | CAC | CAC | CAG | GCG | CTC | GAA | CCC | | 512 |
|---|---|---|---|---|---|---|---|---|---|---|---|---|---|---|---|---|
| Leu | Ala | His | His | His | His | His | His | His | His | Gln | Ala | Leu | Glu | Pro | |  |
|  |  | 100 |  |  |  |  | 105 |  |  |  |  | 110 |  |  |  |  |

| GGC | GAT | CTG | CTG | GAC | CAC | ATC | TCC | TCG | CCG | TCG | CTC | GCG | CTC | ATG | GCC | 560 |
|---|---|---|---|---|---|---|---|---|---|---|---|---|---|---|---|---|
| Gly | Asp | Leu | Leu | Asp | His | Ile | Ser | Ser | Pro | Ser | Leu | Ala | Leu | Met | Ala |  |
|  |  | 115 |  |  |  |  | 120 |  |  |  |  | 125 |  |  |  |  |

| GGC | GCG | GGC | GGC | GCG | GGC | GCG | GCG | GCC | GGC | GGC | GGC | GGC | GCC | CAC | GAC | 608 |
|---|---|---|---|---|---|---|---|---|---|---|---|---|---|---|---|---|
| Gly | Ala | Gly | Gly | Ala | Gly | Ala | Ala | Ala | Gly | Gly | Gly | Gly | Ala | His | Asp |  |
| 130 |  |  |  |  | 135 |  |  |  |  | 140 |  |  |  |  | 145 |  |

| GGC | CCG | GGG | GGC | GGT | GGC | GGC | CCG | GGC | GGC | GGC | GGC | CCG | GGC | GGC | | 656 |
|---|---|---|---|---|---|---|---|---|---|---|---|---|---|---|---|---|
| Gly | Pro | Gly | Gly | Gly | Gly | Gly | Pro | Gly | Gly | Gly | Gly | Pro | Gly | Gly | |  |
|  |  |  |  | 150 |  |  |  |  | 155 |  |  |  |  | 160 |  |  |

| GGC | GGC | CCC | GGG | GGA | GGC | GGC | GGT | GGC | GGC | CCG | GGG | GGC | GGC | GGC | GGC | 704 |
|---|---|---|---|---|---|---|---|---|---|---|---|---|---|---|---|---|
| Gly | Gly | Pro | Gly | Gly | Gly | Gly | Gly | Gly | Gly | Pro | Gly | Gly | Gly | Gly | Gly |  |
|  |  |  |  | 165 |  |  |  |  | 170 |  |  |  |  | 175 |  |  |

| GGC | CCG | GGC | GGC | GGG | CTC | CTG | GGC | GGC | TCC | GCG | CAC | CCT | CAC | CCG | CAT | 752 |
|---|---|---|---|---|---|---|---|---|---|---|---|---|---|---|---|---|
| Gly | Pro | Gly | Gly | Gly | Leu | Leu | Gly | Gly | Ser | Ala | His | Pro | His | Pro | His |  |

```
                        180                              185                              190
ATG  CAC  AGC  CTG  GGC  CAC  CTG  TCG  CAC  CCC  GCG  GCG  GCG  GCC  GCC  ATG        800
Met  His  Ser  Leu  Gly  His  Leu  Ser  His  Pro  Ala  Ala  Ala  Ala  Ala  Met
     195                      200                      205

AAC  ATG  CCG  TCC  GGG  CTG  CCG  CAC  CCC  GGG  CTG  GTG  GCG  GCG  GCG  GCG        848
Asn  Met  Pro  Ser  Gly  Leu  Pro  His  Pro  Gly  Leu  Val  Ala  Ala  Ala  Ala
210                           215                      220                           225

CAC  CAC  GGC  GCG  GCA  GCG  GCA  GCG  GCG  GCG  TCG  GCC  GGG  CAG  GTG             896
His  His  Gly  Ala  Ala  Ala  Ala  Ala  Ala  Ala  Ser  Ala  Gly  Gln  Val
               230                      235                           240

GCA  GCG  GCA  TCG  GCG  GCG  GCG  GCC  GTG  GTG  GGC  GCA  GCG  GGC  CTG  GCG        944
Ala  Ala  Ala  Ser  Ala  Ala  Ala  Ala  Val  Val  Gly  Ala  Ala  Gly  Leu  Ala
               245                      250                           255

TCC  ATC  TGC  GAC  TCG  GAC  ACG  GAC  CCG  CGC  GAG  CTC  GAG  GCG  TTC  GCG        992
Ser  Ile  Cys  Asp  Ser  Asp  Thr  Asp  Pro  Arg  Glu  Leu  Glu  Ala  Phe  Ala
          260                      265                      270

GAG  CGC  TTC  AAG  CAG  CGG  CGC  ATC  AAG  CTG  GGC  GTG  ACG  CAG  GCC  GAC       1040
Glu  Arg  Phe  Lys  Gln  Arg  Arg  Ile  Lys  Leu  Gly  Val  Thr  Gln  Ala  Asp
     275                      280                      285

GTG  GGC  TCG  GCG  CTG  GCC  AAC  CTC  AAG  ATC  CCG  GGC  GTG  GGC  TCA  CTC       1088
Val  Gly  Ser  Ala  Leu  Ala  Asn  Leu  Lys  Ile  Pro  Gly  Val  Gly  Ser  Leu
290                           295                      300                           305

AGC  CAG  AGC  ACC  ATC  TGC  AGG  TTC  GAG  TCG  CTC  ACG  CTC  TCG  CAC  AAC       1136
Ser  Gln  Ser  Thr  Ile  Cys  Arg  Phe  Glu  Ser  Leu  Thr  Leu  Ser  His  Asn
                    310                      315                           320

AAC  ATG  ATC  GCG  CTC  AAG  CCC  ATC  CTG  CAG  GCG  TGG  CTC  GAG  GAG  GCC       1184
Asn  Met  Ile  Ala  Leu  Lys  Pro  Ile  Leu  Gln  Ala  Trp  Leu  Glu  Glu  Ala
               325                      330                           335

GAG  GGC  GCC  CAG  CGC  GAG  AAA  ATG  AAC  AAG  CCT  GAG  CTC  TTC  AAC  GGC       1232
Glu  Gly  Ala  Gln  Arg  Glu  Lys  Met  Asn  Lys  Pro  Glu  Leu  Phe  Asn  Gly
               340                      345                           350

GGC  GAG  AAG  AAG  CGC  AAG  CGG  ACT  TCC  ATC  GCC  GCG  CCC  GAG  AAG  CGC       1280
Gly  Glu  Lys  Lys  Arg  Lys  Arg  Thr  Ser  Ile  Ala  Ala  Pro  Glu  Lys  Arg
     355                      360                      365

TCC  CTC  GAG  GCC  TAC  TTC  GCC  GTG  CAG  CCC  CGG  CCC  TCG  TCC  GAG  AAG       1328
Ser  Leu  Glu  Ala  Tyr  Phe  Ala  Val  Gln  Pro  Arg  Pro  Ser  Ser  Glu  Lys
370                      375                      380                           385

ATC  GCC  GCC  ATC  GCC  GAG  AAA  CTG  GAC  CTC  AAA  AAG  AAC  GTG  GTG  CGG       1376
Ile  Ala  Ala  Ile  Ala  Glu  Lys  Leu  Asp  Leu  Lys  Lys  Asn  Val  Val  Arg
                    390                      395                           400

GTG  TGG  TTT  TGC  AAC  CAG  AGA  CAG  AAG  CAG  AAG  CGG  ATG  AAA  TTC  TCT       1424
Val  Trp  Phe  Cys  Asn  Gln  Arg  Gln  Lys  Gln  Lys  Arg  Met  Lys  Phe  Ser
               405                      410                           415

GCC  ACT  TAC  TGAGGGGGCT  GGGAGGTGTC  GGGCGGGACA  GAATGGGGAG                         1473
Ala  Thr  Tyr
          420

CTGAGGAGGC  ATTTTTGGGG  GGCTTTCCTC  TGCTTGCCTC  CCCTCGGATT  TGGAGTGTCC                1533

GTTATCCTGC  CTGCATTTGG  GGAGTCCCTT  CTCGCTCTCT  TTCCTCCACC  CATTCTCTGA                1593

TTTTCCTGCC  TTTGCTGTCC  CCTAGCCTTG  AGGACTGGGG  TGCTGGGTGT  GGGGATTGGA                1653

GTATAGGGTA  GGGGAGAAGG  GGGGGAGCAT  TCGGGGGAGT  GGGGAGTGGG  GGGAAGGAAA                1713

GCGGAGACCC  GAGCAGGGGT  TTTAAGGAGC  AGGATGGTTC  TGGGGTTTGG  GTGGGGGGAG                1773

ACGCGGGAAG  GGTAGGAAAA  TGGACTGTTT  CTGACCAGAG  ACACTTACCT  AAATATCCTG                1833

GGGACCAAGG  AACTATGTAC  AAAAACAAAC  CTACCAACCA  CCAAAAACTA  GACAAATAAA                1893

GACAAACTAA  AACAAAACAG  AACAAAAGCA  AAGGAAAATG  CTTTAGAAAT  TTTAACTCCG                1953

GGGAGCCATA  ATCTGCAACT  TCATTTTCCC  CCATAGAAGA  GAAAAAAGAG  CACCACCATT                2013
```

```
ATTACCACCT CCCCAACCCT ACACGCACGA ACTGAGTCGA AAAACGAAAA CCAAACGAGC    2073
GAGAAGTTGA AGTTCTGGGT ATCAAAGCTA GTTGTTCTGT CTGCGTGTTT AATTTTTCCC    2133
TCTCTCACCT CCACCCCATC CATATCCTCT TTATTTCCTC CGTTCCAATG AGAGGCCTAT    2193
GGCTGCTCTC CAATCCCGGG AAGTGAGTGG GAGCACAGCT GAAAAGAGAG GGTCAGGGGG    2253
AGGCTGGCTG CTTGCTTAGG TGGAATCCAA GTTTTCCCGT GGCCCTGCCT ATACTCTGGT    2313
GGCCTGGTCC TGTTGGGGTG GGGGTCTTTG GAGAGAAGGG CATAGTCTTT GAGCTACTAA    2373
AAAGCAGAAT TCCGGAGCTT CGAGATATCT TATTCTAGGA AAATGAAACA ATTTTAACAA    2433
CAGTTTTTTT TCCTCTTATG TCGAAGATCT AGTTTTAGAC AATTTCAAAA TAAGCTTTTC    2493
CCACTCATAG AACTTTAACT TGCCCTTTCA GTTTTATCTT TTTTTTAGAG AGAGGTTTAA    2553
ACTACTGATT TTTCCTGTTG ATTCAAATAG ACTAATGGGG TGAAAGTTAT TAGGAGAGAT    2613
ACTCTCTCCT GTTTTCTCCA CTGAACGAGA CTCATCTTGC TCTTCTAGGT CCCGTTTCTT    2673
CCTCTCTTGG AGGACATGAA ATTATAGAAA TGTTGAGAAG TTCCTGCTTT CTTTTGCGGT    2733
AGGACTTGGC TGTGAGAAAA TCACCTAAAT CCCAGAAAAG AGGAAGACAG ATTTAAAGTG    2793
CCCCCACCCC CATTTGTTTC AAAGAGGTCT GCATGTTGGG CGAAAACAGA ACAACTGTGT    2853
TTCCTTTTAC TTGTTCTTAT TATTCAAGAG TCATTTATTA CAGGGGATAA ATGTTGGGTA    2913
GCAAGAACTT TAATTTGCAC TACCAGTCTC CCAAATAGAA AATCATGTAT AGTATTTCAT    2973
AGTAATAATC AGGTACCTTA CAAGCTGCTG GTGGATTTTA AAAAATTAAG ATAGTTGAAG    3033
GTGGTTAGGT AAAATGCCTG CTTTGTGTAC AAGATACTCT TTGGATCTCT CGTAGAGATG    3093
GTTTGTTACC ATCCTTTAAT CATAACTAAA ACATTGAAAA CAGAACAAAT GAGAAAAGAA    3153
AAAAAACCTG CCGATTAACA AGACTGAAAT CATGCATGAT CTGAAGGTG TGGAAAGAAA     3213
CACAATTAGG TCTCACTCTG GTTAGGCATT ATTTATTTAA TTATGTTGTA TATCATTGTT    3273
TGCAGGGCAA ACATTCTATG CATTGAAAC TGAGCACTAA ACTGGGCTAG CTTTCTGGTA     3333
GACCGTTTTG TGGCTAGTGC GATTTCACAG TCTACTGCCT GTTTCCACTG AAAACATTTT    3393
TGTCATATTC TTGTATTCAA AGAAAAGGA AAAAGATTA TTGTAAATAT TTTATTTAAT      3453
GCACACATTC ACACAGTGGT AACAGACTGC CAGTGTTCAT CCTGAAATGT CTCACGGATT    3513
GATCTACCTG TCCATGTATG TCTGCTGAGC TTTCTCCTTG GTTATGTTTT TTCTCTTTTA    3573
CCTTTCTCCT CCCTTACTTC TATCAGAACC AATTCTATGC GCCAAAATAC AACAGGGGA     3633
TGTGTCCCAG TACACTTACA AATAAACAT AACTGAAAGA AGAGCAGTTT TATGATTTGG     3693
GTGCGTTTTT GTGTTTATAC TGGGCCAGGT CCTGGTAGAA CCTTTCAACA AACAACCAAA    3753
CAAAAGAAA ACACAAGAA ATGGGGGAG GGTAGGGTGT TGAAGGGGA CAAAAGGGG         3813
AGAGATTGAG AATGATGTAT TTTTTTGCTG AATCAGAATT CACTTTCAGA TAACTCATGA    3873
AAAGTGGTGC TCTAAATAAA ATGAATTCTA TATTAGTTGC CTGTGTTTAT AAAAGTTATT    3933
ATTTTTTAAC TGCAGAAACT CTTAAACCAC AGCACTTGAT CCAGAGTGGT GAAAACCAAT    3993
AAATAACCAG GCACCCAAAA AAACATTTAA ATTTAGGGTC AGGGACAGAG GAATTTGGAG    4053
GTTTAGATGT GATATTCTAC CCTAAAAACA CCTAGTAACT GAATGGCTTT TCTTTGGAGG    4113
GTAATACATT TTAAAACATT TAGTGTGCCA CCTACTGCTC CACAGTGACT AGAGAGCCTC    4173
TATTTCTTGG TGACTTGGGA CTAGATCAGA TGCCAAATGT ACAAAGTTTC TTAAGAGTTG    4233
AGATTATATC ATCTGAAGTC ATCTTATTTT AGCCAAATCT TTTTAATTTC ACCGGCAAAT    4293
CTGTGAAGGA AAACACTTGA TGTTCAAAAA GAATAGTACA TTTTAAAAGC TGCGATTTTA    4353
AACAGTTGTT AATGTTAAAA AAAAAAAGCA CTAGAGGTAT TTTTAAACAT AGAACTCTTC    4413
```

```
CATAAAAAGT  TGATTTGTTT  TTGCTGTTAT  TGACTTGAAA  CATCATCAGT  TTTAAATAAA      4473

ATGCATTTGT  AAAAAAACCG  TTAAAAAAAA  AAAAAAAAAA  AAAAAAAAAA  A               4524
```

( 2 ) INFORMATION FOR SEQ ID NO:8:

( i ) SEQUENCE CHARACTERISTICS:
    ( A ) LENGTH: 420 amino acids
    ( B ) TYPE: amino acid
    ( D ) TOPOLOGY: linear ( i i ) MOLECULE TYPE: protein ( x i ) SEQUENCE DESCRIPTION: SEQ ID NO:8:

```
Met  Met  Ser  Met  Asn  Ser  Lys  Gln  Pro  His  Phe  Ala  Met  His  Pro  Thr
 1              5                        10                       15

Leu  Pro  Glu  His  Lys  Tyr  Pro  Ser  Leu  His  Ser  Ser  Ser  Glu  Ala  Ile
              20                        25                  30

Arg  Arg  Ala  Cys  Leu  Pro  Thr  Pro  Pro  Leu  Gln  Ser  Asn  Leu  Phe  Ala
              35                        40                  45

Ser  Leu  Asp  Glu  Thr  Leu  Leu  Ala  Arg  Ala  Glu  Ala  Leu  Ala  Ala  Val
     50                       55                  60

Asp  Ile  Ala  Val  Ser  Gln  Gly  Lys  Ser  His  Pro  Phe  Lys  Pro  Asp  Ala
65                            70                  75                       80

Thr  Tyr  His  Thr  Met  Asn  Ser  Val  Pro  Cys  Thr  Ser  Thr  Ser  Thr  Val
                    85                       90                       95

Pro  Leu  Ala  His  His  His  His  His  His  His  His  Gln  Ala  Leu  Glu
              100                      105                      110

Pro  Gly  Asp  Leu  Leu  Asp  His  Ile  Ser  Ser  Pro  Ser  Leu  Ala  Leu  Met
          115                      120                      125

Ala  Gly  Ala  Gly  Gly  Ala  Gly  Ala  Ala  Ala  Gly  Gly  Gly  Gly  Ala  His
     130                      135                      140

Asp  Gly  Pro  Gly  Gly  Gly  Gly  Gly  Pro  Gly  Gly  Gly  Gly  Gly  Pro  Gly
145                      150                      155                      160

Gly  Gly  Gly  Pro  Gly  Gly  Gly  Gly  Gly  Gly  Gly  Pro  Gly  Gly  Gly  Gly
                    165                      170                      175

Gly  Gly  Pro  Gly  Gly  Gly  Leu  Leu  Gly  Gly  Ser  Ala  His  Pro  His  Pro
          180                      185                      190

His  Met  His  Ser  Leu  Gly  His  Leu  Ser  His  Pro  Ala  Ala  Ala  Ala  Ala
          195                      200                      205

Met  Asn  Met  Pro  Ser  Gly  Leu  Pro  His  Pro  Gly  Leu  Val  Ala  Ala  Ala
     210                      215                      220

Ala  His  His  Gly  Ala  Ala  Ala  Ala  Ala  Ala  Ala  Ser  Ala  Gly  Gln
225                      230                      235                      240

Val  Ala  Ala  Ala  Ser  Ala  Ala  Ala  Val  Val  Gly  Ala  Ala  Gly  Leu
                    245                      250                      255

Ala  Ser  Ile  Cys  Asp  Ser  Asp  Thr  Asp  Pro  Arg  Glu  Leu  Glu  Ala  Phe
               260                      265                      270

Ala  Glu  Arg  Phe  Lys  Gln  Arg  Arg  Ile  Lys  Leu  Gly  Val  Thr  Gln  Ala
               275                      280                      285

Asp  Val  Gly  Ser  Ala  Leu  Ala  Asn  Leu  Lys  Ile  Pro  Gly  Val  Gly  Ser
     290                      295                      300

Leu  Ser  Gln  Ser  Thr  Ile  Cys  Arg  Phe  Glu  Ser  Leu  Thr  Leu  Ser  His
305                      310                      315                      320

Asn  Asn  Met  Ile  Ala  Leu  Lys  Pro  Ile  Leu  Gln  Ala  Trp  Leu  Glu  Glu
                    325                      330                      335

Ala  Glu  Gly  Ala  Gln  Arg  Glu  Lys  Met  Asn  Lys  Pro  Glu  Leu  Phe  Asn
```

|     |     |     |     |     |     |     |     |     |     |     |     |     |     |     |
| --- | --- | --- | --- | --- | --- | --- | --- | --- | --- | --- | --- | --- | --- | --- |
|     |     |     | 340 |     |     |     |     | 345 |     |     |     | 350 |     |     |
| Gly | Gly | Glu<br>355 | Lys | Lys | Arg | Lys | Arg<br>360 | Thr | Ser | Ile | Ala | Ala<br>365 | Pro | Glu | Lys |
| Arg | Ser | Leu<br>370 | Glu | Ala | Tyr | Phe<br>375 | Ala | Val | Gln | Pro | Arg<br>380 | Pro | Ser | Ser | Glu |
| Lys<br>385 | Ile | Ala | Ala | Ile | Ala<br>390 | Glu | Lys | Leu | Asp | Leu<br>395 | Lys | Lys | Asn | Val | Val<br>400 |
| Arg | Val | Trp | Phe | Cys<br>405 | Asn | Gln | Arg | Gln | Lys<br>410 | Gln | Lys | Arg | Met | Lys<br>415 | Phe |
| Ser | Ala | Thr | Tyr<br>420 |     |     |     |     |     |     |     |     |     |     |     |     |

( 2 ) INFORMATION FOR SEQ ID NO:9:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:9:

CCAGCGGCTG CAAGGGGACC A          21

( 2 ) INFORMATION FOR SEQ ID NO:10:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: YES ( x i ) SEQUENCE DESCRIPTION: SEQ ID NO:10:

TGCCCGCCGA CCAGGGTGCT          20

( 2 ) INFORMATION FOR SEQ ID NO:11:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:11:

CCCAAGAAGC CCTGAGC          17

( 2 ) INFORMATION FOR SEQ ID NO:12:

( i ) SEQUENCE CHARACTERISTICS:
        ( A ) LENGTH: 21 base pairs
        ( B ) TYPE: nucleic acid (C) STRANDEDNESS: single
(D) TOPOLOGY: linear (i i) MOLECULE TYPE: cDNA (i i i) HYPOTHETICAL: NO (i v) ANTI-SENSE: YES (x i) SEQUENCE DESCRIPTION: SEQ ID NO:12:

CCCTCAAGAA AGGGGAGGGG G 21

(2) INFORMATION FOR SEQ ID NO:13:

(i) SEQUENCE CHARACTERISTICS:
(A) LENGTH: 21 base pairs
(B) TYPE: nucleic acid
(C) STRANDEDNESS: single
(D) TOPOLOGY: linear (i i) MOLECULE TYPE: cDNA (i i i) HYPOTHETICAL: NO (i v) ANTI-SENSE: NO (x i) SEQUENCE DESCRIPTION: SEQ ID NO:13:

CTGATCTAGT CCCAAGTCAC C 21

(2) INFORMATION FOR SEQ ID NO:14:

(i) SEQUENCE CHARACTERISTICS:
(A) LENGTH: 21 base pairs
(B) TYPE: nucleic acid
(C) STRANDEDNESS: single
(D) TOPOLOGY: linear (i i) MOLECULE TYPE: cDNA (i i i) HYPOTHETICAL: NO (i v) ANTI-SENSE: YES (x i) SEQUENCE DESCRIPTION: SEQ ID NO:14:

ACAGCACTTG ATCCAGAGTG G 21

(2) INFORMATION FOR SEQ ID NO:15:

(i) SEQUENCE CHARACTERISTICS:
(A) LENGTH: 19 base pairs
(B) TYPE: nucleic acid
(C) STRANDEDNESS: single
(D) TOPOLOGY: linear (i i) MOLECULE TYPE: cDNA (i i i) HYPOTHETICAL: NO (i v) ANTI-SENSE: NO (x i) SEQUENCE DESCRIPTION: SEQ ID NO:15:

GGCATCGTGA TGGACTCCG 19

(2) INFORMATION FOR SEQ ID NO:16:

(i) SEQUENCE CHARACTERISTICS:
(A) LENGTH: 19 base pairs
(B) TYPE: nucleic acid
(C) STRANDEDNESS: single
(D) TOPOLOGY: linear (i i) MOLECULE TYPE: cDNA ( i i i ) HYPOTHETICAL: NO ( i v ) ANTI-SENSE: YES ( x i ) SEQUENCE DESCRIPTION: SEQ ID NO:16:

```
GCTGGAAGGT  GGACAGCGA                                                        19
```

LEUKEMIA ASSOCIATED GENES

FIELD OF THE INVENTION

This invention relates to nucleic acid molecules and encoded polypeptides which are expressed preferentially in leukemia. The nucleic acid molecules and encoded polypeptides are useful in, inter alia, diagnostic and therapeutic contexts.

BACKGROUND OF THE INVENTION

The phenotypic changes which distinguish a tumor cell from its normal counterpart are often the result of one or more changes to the genome of the cell. The genes which are expressed in tumor cells, but not in normal counterparts, can be termed "tumor specific" genes. These tumor specific genes are markers for the tumor phenotype. The expression of tumor specific genes can also be an essential event in the process of tumorigenesis.

Typically, the host recognizes as foreign the tumor specific genes which are not expressed in normal non-tumorigenic cells. Thus, the expression of tumor specific genes can provoke an immune response against the tumor cells by the host. Tumor specific genes can also be expressed in normal cells within certain tissues without provoking an immune response. In such tissues, expression of the gene and/or presentation of an ordinarily immunologically recognizable fragment of the protein product on the cell surface may not provoke an immune response because the immune system does not "see" the cells inside these immunologically privileged tissues. Examples of immunologically privileged tissues include brain and testis The discovery of tumor specific expression of a gene provides a means of identifying a cell as a tumor cell. Diagnostic compounds can be based on the tumor specific gene, and used to determine the presence and location of tumor cells. Further, when the tumor specific gene contributes to an aspect of the tumor phenotype (e.g., unregulated growth or metastasis), the tumor specific gene can be used to provide therapeutics such as antisense nucleic acids which can reduce or substantially eliminate expression of that gene, thereby reducing or substantially eliminating the phenotypic aspect which depends on the expression of the particular tumor specific gene.

As previously noted, the polypeptide products of tumor specific genes can be the targets for host immune surveillance and provoke selection and expansion of one or more clones of cytotoxic T lymphocytes specific for the tumor specific gene product. Examples of this phenomenon include proteins and fragments thereof encoded by the MAGE family of genes, the tyrosinase gene, the Melan-A gene, the BAGE gene, the GAGE gene, the RAGE family of genes, the PRAME gene and the brain glycogen phosphorylase gene, as are detailed below. Thus, tumor specific expression of genes suggests that such genes can encode proteins which will be recognized by the immune system as foreign and thus provide a target for tumor rejection. Such genes encode "tumor rejection antigen precursors", or TRAPs, which may be used to generate therapeutics for enhancement of the immune system response to tumors expressing such genes and proteins.

The process by which the mammalian immune system recognizes and reacts to foreign or alien materials is a complex one. An important facet of the system is the T cell response. This response requires that T cells recognize and interact with complexes of cell surface molecules, referred to as human leukocyte antigens ("HLA"), or major histocompatibility complexes ("MHCs"), and peptides. The peptides are derived from larger molecules which are processed by the cells which also present the HLA/MHC molecule. See in this regard Male et al., *Advanced Immunology* (J.P. Lipincott Company, 1987), especially chapters 6–10. The interaction of T cells and complexes of HLA/peptide is restricted, requiring a T cell specific for a particular combination of an HLA molecule and a peptide. If a specific T cell is not present, there is no T cell response even if its partner complex is present. Similarly, there is no response if the specific complex is absent, but the T cell is present. The mechanism is involved in the immune system's response to foreign materials, in autoimnmune pathologies, and in responses to cellular abnormalities. Much work has focused on the mechanisms by which proteins are processed into the HLA binding peptides. See, in this regard, Barinaga, *Science* 257: 880, 1992; Fremont et al., *Science* 257: 919, 1992; Matsumura et al., *Science* 257: 927, 1992; Latron et al., *Science* 257: 964, 1992.

The mechanism by which T cells recognize cellular abnormalities has also been implicated in cancer. For example, in PCT application PCT/US92/04354, filed May 22, 1992, published on Nov. 26, 1992, and incorporated by reference, a family of genes is disclosed, which are processed into peptides which, in turn, are expressed on cell surfaces, which can lead to lysis of the tumor cells by specific CTLs. The genes are said to code for "tumor rejection antigen precursors" or "TRAP" molecules, and the peptides derived therefrom are referred to as "tumor rejection antigens" or "TRAs". See Traversari et al., *J. Exp. Med.* 176:1453–1457, 1992; van der Bruggen et al., *Science* 254: 1643,1991; De Plaen et al., *Immunogenetics* 40:360–369, 1994 for further information on this family of genes. Also, see U.S. patent application Ser. No. 807,043, filed Dec. 12, 1991, now U.S. Pat. No. 5,342,774.

In U.S. patent application Ser. No. 938,334, now U.S. Pat. No. 5,405,940, the disclosure of which is incorporated by reference, nonapeptides are taught which are presented by the HLA-A1 molecule. The reference teaches that given the known specificity of particular peptides for particular HLA molecules, one should expect a particular peptide to bind one HLA molecule, but not others. This is important, because different individuals possess different HLA phenotypes. As a result, while identification of a particular peptide as being a partner for a specific HLA molecule has diagnostic and therapeutic ramifications, these are only relevant for individuals with that particular HLA phenotype. There is a need for further work in the area, because cellular abnormalities are not restricted to one particular HLA phenotype, and targeted therapy requires some knowledge of the phenotype of the abnormal cells at issue.

In U.S. patent application Ser. No. 008,446, filed Jan. 22, 1993 and incorporated by reference, the fact that the MAGE-1 expression product is processed to a second TRA is disclosed. This second TRA is presented by HLA-Cw16 molecules, also known as HLA-C*1601. The disclosure shows that a given TRAP can yield a plurality of TRAs.

In U.S. patent application Ser. No. 994,928, filed Dec. 22, 1992, and incorporated by reference herein, tyrosinase is described as a tumor rejection antigen precursor. This reference discloses that a molecule which is produced by some normal cells (e.g., melanocytes), is processed in tumor cells to yield a tumor rejection antigen that is presented by HLA-A2 molecules.

In U.S. patent application Ser. No. 08/032,978, now U.S. Pat. No. 5,620,886, and incorporated herein by reference in its entirety, a second TRA, not derived from tyrosinase is taught to be presented by HLA-A2 molecules. The TRA is derived from a TRAP, but is coded for by a known MAGE gene. This disclosure shows that a particular HLA molecule may present TRAs derived from different sources.

In U.S. patent application Ser. No. 079,110, now U.S. Pat. No. 5,571,711 and entitled "Isolated Nucleic Acid Molecules Coding For BAGE Tumor Rejection Antigen Precursors" and Ser. No. 196,630, filed Feb. 15, 1994, and entitled "Isolated Peptides Which form Complexes with MHC Molecule HLA-C-Clone 10 and Uses Thereof" the entire disclosures of which are incorporated herein by reference, an unrelated tumor rejection antigen precursor, the so-called "BAGE" precursor, is described. TRAs are derived from the TRAP and also are described. They form complexes with MHC molecule HLA-C-Clone 10.

In U.S. patent application Ser. No. 096,039, filed Jul. 22, 1993 and entitled "Isolated Nucleic Acid Molecules Coding for GAGE Tumor Rejection Antigen Precursors" and Ser. No. 250,162, now U.S. Pat. No. 5,610,013 and entitled "Method for Diagnosing a Disorder by Determining Expression of GAGE Tumor Rejection Antigen Precursors", the entire disclosures of which are incorporated herein by reference, another unrelated tumor rejection antigen precursor, the so-called "GAGE" precursor, is described. The GAGE precursor is not related to the BAGE or the MAGE family.

In U.S. patent application Ser. No. 08/408,015, filed Mar. 21, 1995, and entitled "RAGE Tumor Rejection Antigen Precursors", incorporated herein by reference in its entirety, another TRAP is taught which is not derived from any of the foregoing genes. The TRAP is referred to as RAGE. In U.S. patent application Ser. No. 08/530,015, filed Sep. 20, 1995, and entitled "Isolated RAGE-1 Derived Peptides Which Complex with HLA-B7 Molecules and Uses Thereof", also incorporated by reference, the TRA derived form one member of the RAGE family of genes is taught to be presented by HLA-B7 molecules. This disclosure shows that additional TRAPs and TRAs can be derived from different sources.

In U.S. patent application Ser. no. 08/253,503, now U.S. Pat. No. 5,589,334, and entitled "Isolated Nucleic Acid Molecule Which Codes for a Tumor Rejection Antigen Precursor Which is Processed to an Antigen Presented by HLA-B44", incorporated herein by reference in its entirety, another TRAP is taught which is not derived from any of the foregoing genes. The gene encoding the TRAP is referred to as MUM-1. A tumor rejection antigen, LB-33B, is described in the application.

In U.S. patent application Ser. No. 08/373,636, filed Jan. 17, 1995, and entitled "Isolated Nucleic Acid Molecule Which Codes for a Tumor Rejection Antigen Precursor Which is Processed to Antigens Presented by HLA Molecules and Uses Thereof", incorporated herein by reference in its entirety, other TRAPs are taught which are derived from LB33 and presented by HLA-B13, HLA-Cw6, HLA-A28 and HLA-A24.

In PCT publication WO96/10577, published Apr. 11, 1996, and entitled "Isolated Nucleic Acid Molecule Coding for a Tumor Rejection Antigen Precursor DAGE and Uses Thereof", incorporated herein by reference in its entirety, another TRAP is taught which is not derived from any of the foregoing genes. The TRAP was referred to as DAGE, but is now referred to as PRAME. A tumor rejection antigen is described in the application which is presented by HLA-A24.

In U.S. patent application Ser. No. 08/487,135, filed Jun. 7, 1995, and entitled "Isolated Nucleic Acid Molecule, Peptides Which Form Complexes with MHC Molecule HLA-A2 and Uses Thereof", incorporated herein by reference in its entirety, another TRAP is taught which is not derived from any of the foregoing genes. The TRAP is referred to as NAG. Various TRAs derived from NAG and presented by HLA-A2 are taught in this application.

In U.S. patent application Ser. No. 08/403,388, now U.S. Pat. No. 5,587,289, and entitled "Isolated Nucleic Acid Molecules Which Are Members of the MAGE-Xp Family and Uses Thereof", incorporated herein by reference in its entirety, three TRAPs are taught which are not derived from any of the foregoing genes. These TRAPs are referred to as MAGE-Xp2, MAGE-Xp3 and MAGE-Xp4.

The work which is presented by the papers, patents and patent applications described above deal, for the most part, with the MAGE family of genes, the BAGE gene, the GAGE gene and the RAGE family of genes.

In U.S. patent application Ser. No. 08/672,351, filed Jun. 25, 1996, and entitled "Brain Glycogen Phosphorylase Cancer Antigen", incorporated herein by reference in its entirety, another TRAP is taught which is not derived from any of the foregoing genes. This TRAP is a gene which is expressed normally in the brain and retinal pigmented epithelium. It was discovered that the brain glycogen phosphorylase gene is expressed in melanoma cells, and encodes tumor rejection antigens and precursors thereof. It now has been discovered that additional genes similarly are expressed in a tumor associated pattern in leukemia cells.

These three genes which are believed to encode tumor rejection antigen precursors are referred to generally as leukemia associated genes. These genes do not show homology to the MAGE family of genes, to the BAGE gene, the GAGE gene, the RAGE family of genes, the LB33/MUM-1 gene, the NAG gene, the MAGE-Xp family of genes or the brain glycogen phosphorylase gene. Two of the genes are known genes which were not previously known to be expressed in a leukemia associated manner. One of the genes is an unknown gene. Thus the invention relates to the genes expressed specifically in certain leukemia cells, tumor rejection antigen precursors encoded by such genes, as well as related molecules and applications of these various entities.

The invention is elaborated upon further in the disclosure which follows.

SUMMARY OF THE INVENTION

The invention provides isolated nucleic acid molecules encoding leukemia associated polypeptides. The invention also provides expression vectors containing those molecules and host cells transfected with those molecules, as well as isolated polypeptides encoded by the leukemia associated nucleic acid molecules and fragments of the isolated polypeptides. The foregoing isolated nucleic acid molecules and polypeptides can be used in the diagnosis or treatment of conditions characterized by the expression of a leukemia associated gene.

According to one aspect of the invention, methods for diagnosing a disorder characterized by the expression of a leukemia associated nucleic acid molecule or a leukemia associated polypeptide are provided. The methods involve contacting a biological sample isolated from a subject with an agent that is specific for the leukemia associated nucleic acid molecule or an expression product thereof. In certain embodiments, the leukemia associated nucleic acid molecule hybridizes under stringent conditions to a molecule having a nucleotide sequence selected from the group consisting of SEQ ID NO:1, SEQ ID NO:3, SEQ ID NO:5, and SEQ ID NO:7. In these certain embodiments, the leukemia associated nucleic acid optionally codes for a leukemia associated polypeptide. In other embodiments, the agent is a binding agent which selectively binds to a leukemia associated polypeptide, such as an antibody, cytotoxic T lymphocyte, polypeptide, and the like. The methods further involve determining the interaction or binding between the agent and the nucleic acid molecule or expression product thereof as a determination of the disorder. In preferred embodiments, the agent is a nucleic acid molecule comprising a molecule having a nucleotide sequence selected from the group consisting of SEQ ID NO:1, SEQ ID NO:3, SEQ ID NO:5, SEQ ID NO:7, fragments thereof, and complements thereof. In certain embodiments, the interaction between the agent and the nucleic acid molecule is determined by amplifying at least a portion of the nucleic acid molecule. In other preferred embodiments, the leukemia associated polypeptide comprises a polypeptide having an amino acid sequence selected from the group consisting of SEQ ID NO:2, SEQ ID NO:4, SEQ ID NO:6, SEQ ID NO:8 and fragments thereof. In particularly preferred embodiments, the agent which binds the leukemia associated polypeptide is an antibody. In the foregoing embodiments, the biological sample preferably is isolated from a non-fetal-brain tissue, a non-mastocyte tissue, or a non-fetal-testis tissue. In certain of the foregoing embodiments, the leukemia associated nucleic acids and polypeptides are fragments of the foregoing sequences.

The recognition that peptides derived from leukemia associated polypeptides may be presented by HLA molecules and recognized by CTLs permits diagnosis of certain disorders. Thus, according to another aspect of the invention, a method for diagnosis of a disorder characterized by expression of a tumor rejection antigen derived from a leukemia associated polypeptide is provided. The method involves contacting a biological sample isolated from a subject with an agent that is specific for the tumor rejection antigen derived from a leukemia associated polypeptide. The method then provides for determining the interaction between the agent and the tumor rejection antigen derived from a leukemia associated polypeptide as a determination of the disorder. In certain embodiments, the tumor rejection antigen derived from a leukemia associated polypeptide comprises the amino acid sequence of a fragment of SEQ ID NO:2, SEQ ID NO:4, SEQ ID NO:6 or SEQ ID NO:8. In preferred embodiments, the tumor rejection antigen comprises between 7 and 100 consecutive amino acids of the foregoing sequences. Preferably, the biological sample is isolated from non-fetal-brain, non-mastocyte or non-fetal testis tissue. In certain embodiments, the agent is an antibody.

The above-described method provides diagnosis of a disorder based on the presence of leukemia associated TRAs. Another aspect of the invention provides methods for diagnosing a disorder characterized by the expression of a tumor rejection antigen derived from a leukemia associated polypeptide which forms a complex with HLA molecules. The method involves contacting a biological sample isolated from a subject with an agent that binds the complex and then determining binding between the complex and the agent as a determination of the disorder. In one embodiment, the tumor rejection antigen derived from a leukemia associated polypeptide is a peptide comprising the amino acids of a fragment of SEQ ID NO:2, SEQ ID NO:4, SEQ ID NO:6 or SEQ ID NO:8. In preferred embodiments, the tumor rejection antigen comprises between 7 and 100 consecutive amino acids of the foregoing sequences. Preferably, the biological sample is isolated from non-fetal-brain, non-mastocyte or non-fetal testis tissue. In certain embodiments, the agent is an antibody.

In addition to diagnosis of disorders, treatment of certain disorders is also desirable. According to another aspect of the invention, methods for treating a subject with a disorder characterized by expression of a leukemia associated nucleic acid or polypeptide is provided. The method involves administering to the subject an agent which reduces the expression of the leukemia associated nucleic acid or polypeptide to ameliorate the disorder. The agent is administered in an effective amount. In certain embodiments, the leukemia associated nucleic acid or polypeptide is a tumor rejection antigen and the method involves administering to the subject an amount of an agent which enriches selectively in the subject the presence of complexes of HLA and a tumor rejection antigen derived from a leukemia associated polypeptide encoded by a nucleic acid molecule selected from the group consisting of SEQ ID NO:1, SEQ ID NO:3, SEQ ID NO:5 and SEQ ID NO:7, sufficient to ameliorate the disorder. Preferably, the tumor rejection antigen derived from a leukemia associated polypeptide is a peptide derived from the polypeptide of SEQ ID NO:2, SEQ ID NO:4, SEQ ID NO:6 or SEQ ID NO:8. Another method involves administering to a subject in need of such treatment an amount of autologous cytolytic T cells sufficient to ameliorate the disorder, wherein the autologous cytolytic T cells are specific for complexes of an HLA molecule and a tumor rejection antigen derived from a leukemia associated polypeptide. Preferably the complexes are formed of HLA and the certain leukemia associated peptides as described above. In other embodiments, the leukemia associated nucleic acid or polypeptide is a nucleic acid and the agent is an antisense nucleic acid. The antisense nucleic acid preferably hybridizes to a leukemia associated nucleic acid selected from the group consisting of SEQ ID NO:1, SEQ ID NO:3, SEQ ID NO:5, SEQ ID NO:7 and fragments thereof.

According to another aspect of the invention, a composition is provided. The composition comprises an antisense nucleic acid which binds to a leukemia associated nucleic acid selected from the group consisting of SEQ ID NO:1, SEQ ID NO:3, SEQ ID NO:5, SEQ ID NO:7 and fragments thereof. The antisense nucleic acid reduces the expression of the leukemia associated nucleic acid. The composition also includes a pharmaceutically acceptable carrier.

The invention in another aspect involves a kit for detecting the presence of the expression of a leukemia associated polypeptide precursor. Such kits employ two or more of the above-described nucleic acid molecules isolated in separate containers and packaged in a single package. In one such kit, a pair of isolated nucleic acid molecules is provided, each of the pair consisting essentially of a molecule selected from the group consisting of a 12–32 nucleotide contiguous segment of SEQ ID NO:1 and complements thereof, a 12–32 nucleotide contiguous segment of SEQ ID NO:3 and complements thereof, a 12–32 nucleotide contiguous segment of SEQ ID NO:5, a 12–32 nucleotide contiguous segment of SEQ ID NO:7 and complements thereof, and wherein the contiguous segments are nonoverlapping. Preferably, the pair of isolated nucleic acid molecules is constructed and arranged to selectively amplify at least a portion of an isolated nucleic acid molecule which hybridizes under stringent conditions to a molecule selected from the group consisting of the nucleic acid sequence of SEQ ID NO:1, the nucleic acid sequence of SEQ ID NO:3, the nucleic acid sequence of SEQ ID NO:5, the nucleic acid sequence of SEQ ID NO:7, nucleic acid molecules which differ from the above in codon sequence due to the degeneracy of the genetic code and complements thereof. In certain embodiments, the pair of isolated nucleic acid molecules is PCR primers. Preferably one of the primers is a contiguous segment of SEQ ID NO:1 and another of the primers is a complement of another contiguous segment of SEQ ID NO:1. In other preferred embodiments, one of the primers is a contiguous segment of SEQ ID NO:3 and another of the primers is the complement of another contiguous segment of SEQ ID NO:3. In still other preferred embodiments, one of the primers is a contiguous segment of SEQ ID NO:5 and another of the primers is the complement of another contiguous segment of SEQ ID NO:5. In yet other preferred embodiments, one of the primers is a contiguous segment of SEQ ID NO:7 and another of the primers is the complement of another contiguous segment of SEQ ID NO:7.

The invention in another aspect also provides pharmaceutical preparations containing the agents and/or cells of the preceding paragraphs. In one embodiment, the preparation contains a pharmaceutically effective amount of preproTRH, tryptase-L, Oct-T1 or a fragment thereof that binds an HLA molecule along with pharmaceutically acceptable diluents, carriers or excipients. In another embodiment, the preparation contains a pharmaceutically effective amount of isolated autologous cytolytic T cells specific for complexes of an HLA molecule and a tumor rejection antigen derived from preproTRH, tryptase-L or Oct-T1.

According to another aspect of the invention, the use of isolated preproTRH, tryptase-L, Oct-T1 or fragments thereof in the manufacture of a medicament is provided. Preferred fragments of the preproTRH, tryptase-L and Oct-T1 molecules are described above. The use of antisense nucleic acids which bind to a leukemia associated nucleic acid in the manufacture of a medicament is also provided. In certain embodiments, the medicament is an injectable medicament, an oral medicament, or an inhalable medicament.

According to another aspect of the invention, the use of isolated preproTRH, tryptase-L, Oct-T1 or fragments thereof, including antisense nucleic acids, in the manufacture of a medicament for the treatment of cancer is provided.

According to still another aspect of the invention, an isolated nucleic acid molecule is provided. The molecule hybridizes under stringent conditions to a nucleic acid having a nucleotide sequence selected from the group consisting of SEQ ID NO:3 or SEQ ID NO:5. The isolated nucleic acid molecule is a leukemia associated polypeptide precursor and codes for a tryptase-L leukemia associated polypeptide. The invention further embraces nucleic acid molecules that differ from the foregoing isolated nucleic acid molecules in codon sequence to the degeneracy of the genetic code. The invention also embraces complements of the foregoing nucleic acids. In preferred embodiments, the isolated nucleic acid molecule comprises the nucleic acid sequence of SEQ ID NO:3 or SEQ ID NO:5. In particularly preferred embodiments, the isolated nucleic acid molecule comprises the coding region of the foregoing nucleic acids.

According to another aspect of the invention, an isolated nucleic acid molecule is provided which comprises a molecule selected from the group consisting of a unique fragment of nucleotides 487–1499 of SEQ ID NO:3 or SEQ ID NO:5 between 12 and 1012 nucleotides in length, a unique fragment of nucleotides 1665–1774 of SEQ ID NO:5 between 12 and 109 nucleotides in length and complements thereof. In preferred embodiments, the unique fragment is at least 14, 15, 16, 17, 18, 20 or 22 contiguous nucleotides of the foregoing. In another embodiment, the isolated nucleic acid molecule consists of between 12 and 32 contiguous nucleotides of the foregoing.

According to yet another aspect of the invention, the invention involves expression vectors, and host cells transformed or transfected with such expression vectors, comprising the nucleic acid molecules described above. The expression vectors optionally include a nucleic acid molecule which codes for an HLA molecule. Of course, an HLA-encoding nucleic acid molecule can also be contained in a separate expression vector. Host cells transformed or transfected with the foregoing expression vectors are also provided.

According to another aspect of the invention, an isolated tryptase-L polypeptide is provided which is encoded by a nucleic acid molecule which hybridizes under stringent conditions to a molecule having the nucleic acid sequence of SEQ ID NO:3, the nucleic acid sequence of SEQ ID NO:5, nucleic acid molecules which vary from the foregoing according to the degeneracy of the genetic code, and complements of any of the foregoing nucleic acid molecules.

According to yet another aspect of the invention, an isolated polypeptide is provided which comprises a unique fragment of SEQ ID NO:4 or SEQ ID NO:6 between 9 and 189 amino acids in length. Preferably, the unique fragment of the isolated polypeptide binds to a polypeptide-binding agent. In other preferred embodiments, the unique fragment of the isolated polypeptide binds to an antibody or a cytotoxic T lymphocyte.

The invention also provides isolated polypeptides which selectively bind a tryptase-L protein or fragments thereof. Isolated binding polypeptides include antibodies and fragments of antibodies (e.g., Fab, F(ab)$_2$, Fd and antibody fragments which include a CDR3 region which binds selectively to the tryptase-L proteins of the invention). The isolated binding polypeptides include monoclonal antibodies.

In connection with any of the isolated nucleic acids encoding a leukemia associated polypeptide as described above, especially a tumor rejection antigen derived from a leukemia associated polypeptide, the invention also embraces degenerate nucleic acids that differ from the isolated nucleic acid in codon sequence only due to the degeneracy of the genetic code or complements of any of the foregoing nucleic acids.

The invention also embraces functional variants and equivalents of all of the molecules described above.

These and other objects of the invention will be described in fuirther detail in connection with the detailed description of the invention.

BRIEF DESCRIPTION OF THE SEQUENCES

Figure 1:
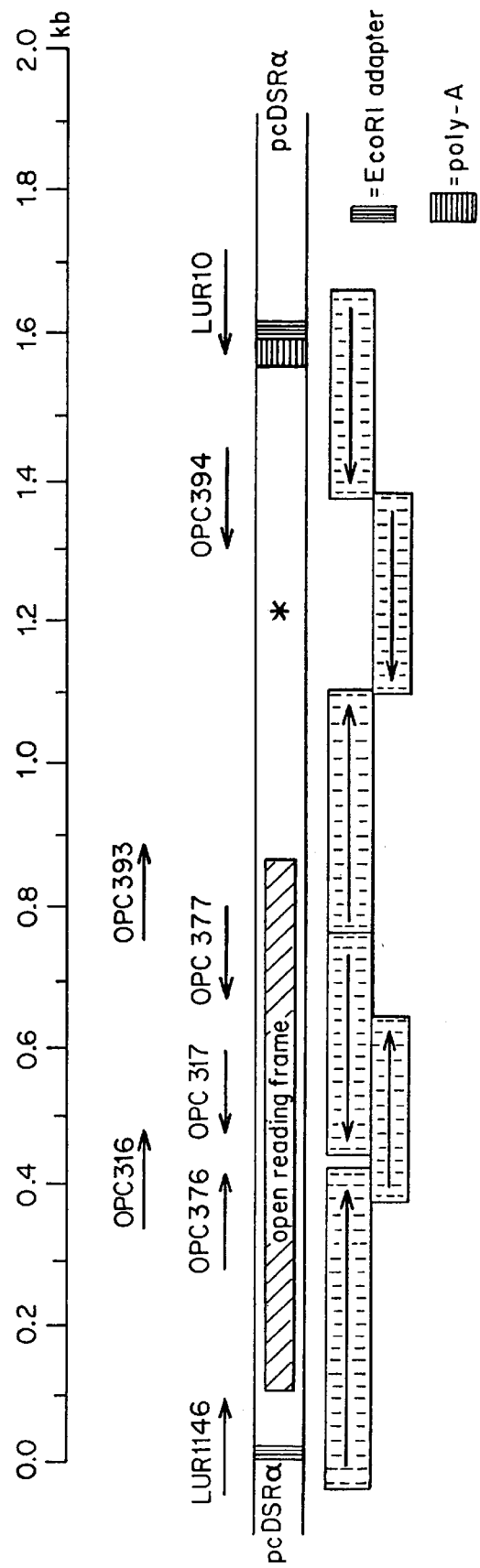
FIG. 1 is a schematic drawing which depicts the sequencing of preproTRH.

SEQ ID NO:1 is the nucleotide sequence of the preproTRH gene.

SEQ ID NO:2 is the amino acid sequence of the polypeptide encoded by the preproTRH gene.

SEQ ID NO:3 is the nucleotide sequence of the tryptase-L gene clone NVB352/1.

SEQ ID NO:4 is the amino acid sequence of the polypeptide encoded by the tryptase-L gene clone NVB352/1.

SEQ ID NO:5 is the nucleotide sequence of the tryptase-L gene clone NVB352/3.

SEQ ID NO:6 is the amino acid sequence of the polypeptide encoded by the tryptase-L gene clone NVB352/3.

SEQ ID NO:7 is the nucleotide sequence of the SIAX DP2-64 (Oct-T1) gene.

SEQ ID NO:8 is the amino acid sequence of the polypeptide encoded by the SIAX DP2-64 (Oct-T1) gene.

SEQ ID NO:9 is a sense primer for specific PCR amplification of preproTRH.

SEQ ID NO:10 is an antisense primer for specific PCR amplification of preproTRH.

SEQ ID NO:11 is a sense primer for specific PCR amplification of tryptase-L.

SEQ ID NO:12 is an antisense primer for specific PCR amplification of tryptase-L.

SEQ ID NO:13 is a sense primer for specific PCR amplification of SIAX DP2-64 (Oct-T1).

SEQ ID NO:14 is an antisense primer for specific PCR amplification of SIAX DP2-64 (Oct-T1).

SEQ ID NO:15 is a sense primer for specific PCR amplification of β-actin.

SEQ ID NO:16 is an antisense primer for specific PCR amplification of β-actin.

DETAILED DESCRIPTION OF THE INVENTION

The examples which follow show the isolation of nucleic acid molecules which code for polypeptides and are expressed preferentially in malignant hemopathies, i.e. which are leukemia associated genes. These isolated nucleic acid molecules include nucleic acid molecules which encode preproTRH, tryptase-L and Oct-T1. In particular, the tryptase-L nucleic acids are different from previously disclosed tryptase coding sequences described supra. Hence, one aspect of the invention is an isolated nucleic acid molecule which includes all or a unique portion of the nucleotide sequence set forth in SEQ ID NO:3 or SEQ ID NO:5. This sequence, and the other leukemia associated gene sequences do not encode a previously recognized tumor rejection antigen precursor, such as a MAGE, BAGE, GAGE, RAGE, LB33/MUM-1, PRAME, NAG, MAGE-Xp or brain glycogen phosphorylase sequence, as will be seen by comparing them to the sequence of any of the genes described in the references.

The invention thus involves in one aspect preproTRH, tryptase-L and Oct-T1 nucleic acids, encoded polypeptides, functional modifications and variants of the foregoing, useful fragments of the foregoing, as well as therapeutics and diagnostics related thereto.

According to one aspect of the invention, methods for diagnosing a disorder that is characterized by expression of a leukemia associated nucleic acid or polypeptide are provided. The methods involve contacting a biological sample isolated from a subject with an agent specific for the leukemia associated nucleic acid or polypeptide to detect the presence of the leukemia associated nucleic acid or polypeptide in the biological sample. As used herein, "contacting" means placing the biological sample in sufficient proximity to the agent and under the appropriate conditions of, e.g., concentration, temperature, time, ionic strength, to allow the specific interaction between the agent and leukemia associated nucleic acid or polypeptide that are present in the biological sample. In general, the conditions for contacting the agent with the biological sample are conditions known by those of ordinary skill in the art to facilitate a specific interaction between a molecule and its cognate (e.g., a protein and its receptor cognate, an antibody and its protein antigen cognate, a nucleic acid and its complementary sequence cognate) in a biological sample. Exemplary conditions for facilitating a specific interaction between a molecule and its cognate are described in U.S. Pat. No. 5,108,921, issued to Low et al.

The biological sample can be located in vivo or in vitro. For example, the biological sample can be a hematopoietic tissue in vivo and the agent specific for the leukemia associated nucleic acid or polypeptide can be used to detect the presence of such molecules in the hematopoietic tissue (e.g., for imaging portions of the hematopoietic tissue that express the leukemia associated gene products). Alternatively, the biological sample can be located in vitro (e.g., a blood sample, bone marrow biopsy, tissue extract). In a particularly preferred embodiment, the biological sample can be a cell-containing sample, more preferably a sample containing hematopoietic cells.

Also a part of the invention are those nucleic acid sequences which also code for a preproTRH, tryptase-L or Oct-T1 polypeptide and which hybridize under stringent conditions to a nucleic acid molecule consisting of the nucleotide sequence set forth in SEQ ID NO:1, SEQ ID NO:3, SEQ ID NO:5 or SEQ ID NO:7, respectively. Such nucleic acids are termed leukemia associated polypeptide precursors, and may be DNA, RNA, or composed of mixed deoxyribonucleotides and ribonucleotides. The leukemia associated polypeptide precursors can also incorporate synthetic non-natural nucleotides.

The invention thus encompasses other leukemia associated nucleic acids, some of which previously were identified in normal tissues. A leukemia associated nucleic acid or polypeptide is a nucleic acid or polypeptide expressed preferentially in leukemias and solid forms of leukemia cell malignancies, such as lymphomas. Various methods for determining the expression of a nucleic acid and/or a polypeptide in normal and leukemia cells are known to those of skill in the art and are described further below. As used herein, leukemia associated polypeptides include proteins, protein fragments, and peptides. In particular, leukemia associated polypeptides include TRAPs and TRAs.

The term "stringent conditions" as used herein refers to parameters with which the art is familiar. More specifically, stringent conditions, as used herein, refers to hybridization at 65° C. in hybridization buffer (3.5×SSC, 0.02% Ficoll, 0.02% polyvinyl pyrolidone, 0.02% Bovine Serum Albumin, 25 mM NaH$_2$PO$_4$ (pH 7), 0.5% SDS, 2 mM EDTA). SSC is 0.15M sodium chloride/0.15M sodium citrate, pH 7; SDS is sodium dodecyl sulphate; and EDTA is ethylenediaminetetracetic acid. After hybridization, the membrane upon which the nucleic acid is transferred is washed at 2×SSC at room temperature and then at 0.1×SSC/

0.1×SDS at 65° C. SSC is 0.15M sodium chloride/0.15M sodium citrate, pH 7; SDS is sodium dodecyl sulphate; and EDTA is ethylenediamine tetraacetic acid.

There are other conditions, reagents, and so forth which can be used, which result in the same degree of stringency (see, e.g. *Molecular Cloning: A Laboratory Manual*, J. Sambrook, et al., eds., Second Edition, Cold Spring Harbor Laboratory Press, Cold Spring Harbor, N.Y., 1989, or *Current Protocols in Molecular Biology*, F. M. Ausubel, et al., eds., John Wiley & Sons, Inc., New York). The skilled artisan will be familiar with such conditions, and thus they are not given here. It will be understood, however, that the skilled artisan will be able to manipulate the conditions in a manner to permit the clear identification of homologs and alleles of tryptase-L nucleic acid molecules of the invention. The skilled artisan also is familiar with the methodology for screening cells, preferably cancer cells, and libraries for expression of such molecules which then are routinely isolated, followed by isolation of the pertinent nucleic acid and sequencing.

In general homologs and alleles typically will share at least 40% nucleotide identity and/or at least 50% amino acid identity to the coding region of leukemia associated nucleic acids, in some instances will share at least 50% nucleotide identity and/or at least 65% amino acid identity and in still other instances will share at least 60% nucleotide identity and/or at least 75% amino acid identity. Watson-Crick complements of the foregoing nucleic acids also are embraced by the invention.

The nucleic acids disclosed herein are useful for determining the expression of preproTRH, tryptase-L and Oct-T1 genes according to standard hybridization procedures. The nucleic acids also can be used to express leukemia associated polypeptides in vitro or in vivo. The nucleic acids also can be used to prepare fragments of such polypeptides useful for e.g., preparation of antibodies. Many other uses will be apparent to the skilled artisan.

In screening for related genes, such as tryptase-L family members, a Southern blot may be performed using the foregoing conditions, together with a radioactive probe. After washing the membrane to which the nucleic acid is finally transferred, the membrane can be placed against x-ray film to detect the radioactive signal.

The invention also includes degenerate nucleic acids which include alternative codons to those present in the native materials. For example, serine residues are encoded by the codons TCA, AGT, TCC, TCG, TCT and AGC. Each of the six codons is equivalent for the purposes of encoding a serine residue. Thus, it will be apparent to one of ordinary skill in the art that any of the serine-encoding nucleotide triplets may be employed to direct the protein synthesis apparatus, in vitro or in vivo, to incorporate a serine residue. Similarly, nucleotide sequence triplets which encode other amino acid residues include, but are not limited to: CCA, CCC, CCG and CCT (proline codons); CGA, CGC, CGG, CGT, AGA and AGG (arginine codons); ACA, ACC, ACG and ACT (threonine codons); AAC and AAT (asparagine codons); and ATA, ATC and ATT (isoleucine codons). Other amino acid residues may be encoded similarly by multiple nucleotide sequences. Thus, the invention embraces degenerate nucleic acids that differ from the biologically isolated nucleic acids in codon sequence due to the degeneracy of the genetic code.

The invention also provides isolated unique fragments of SEQ ID NO:1, SEQ ID NO:3, SEQ ID NO:5, SEQ ID NO:7 or complements thereof. A unique fragment is one that is a 'signature' for the larger nucleic acid. It is, for example, long enough to assure that its precise sequence is not found in molecules outside of the tryptase-L family as defined herein. Unique fragments can be used as probes in Southern blot assays to identify family members or can be used in amplification assays such as those employing PCR. As known to those skilled in the art, large probes such as 200 nucleotides or more are preferred for certain uses such as Southern blots, while smaller fragments will be preferred for uses such as PCR. Unique fragments also can be used to produce fusion proteins for generating antibodies or for generating immunoassay components. Unique fragments further can be used as antisense molecules to inhibit the expression of the leukemia associated nucleic acids and encoded proteins of the invention, particularly for therapeutic purposes as described in greater detail below.

As will be recognized by those skilled in the art, the size of the unique fragment will depend upon its conservancy in the genetic code. Thus, some regions of SEQ ID NO:1, SEQ ID NO:3, SEQ ID NO:5, SEQ ID NO:7 and complements thereof will require longer segments to be unique while others will require only short segments, typically between 12 and 32 nucleotides (e.g. 12, 13, 14, 15, 16, 17, 18, 19, 20, 21, 22, 23, 24, 25, 26, 27, 28, 29, 30, 31 and 32 nucleotides long). Those skilled in the art are well versed in methods for selecting such sequences, typically on the basis of the ability of the unique fragment to selectively distinguish the sequence of interest from non-family members. A comparison of the sequence of the fragment to those on known data bases typically is all that is necessary, although in vitro confirmatory hybridization and sequencing analysis may be performed.

For any pair of PCR primers constructed and arranged to selectively amplify, for example, a tryptase-L nucleic acid, a tryptase-L specific primer may be used. Such a primer is a contiguous stretch of tryptase-L which hybridizes selectively to tryptase-L and not other tryptase nucleic acids. Such a specific primer would fully hybridize to a contiguous stretch of nucleotides only in tryptase-L, but would hybridize at most only in part to tryptase genes that do not share the nucleotides to which the tryptase-L specific primer binds. For efficient PCR priming and tryptase-L identification, the tryptase-L specific primer should be constructed and arranged so it does not hybridize efficiently at its 3' end to tryptase genes other than tryptase-L. Preferably the area of non-identity is at least one to four nucleotides in length and forms the 3' end of the tryptase-L specific primer. The kinetics of hybridization then will strongly favor hybridization at the 5' end. In this instance, 3' initiated PCR extension will occur only when both the 5' and 3' ends hybridize to the nucleic acid. Primers for selective amplification of tryptase-L preferably are selected from portions of SEQ ID NO:3 which share lesser homology with tryptases other than tryptase-L. In such cases, selective amplification of tryptase-L can be achieved with one tryptase-L specific primer and one primer which hybridizes to tryptases generically. Preferably, however, both primers are tryptase-L specific primers are described hereinabove. Exemplary primers include SEQ ID NO:11 and SEQ ID NO:12, which are derived from SEQ ID NO:3, respectively. Other exemplary primers can differ from the above by addition or deletion of 1, 2, 3, 4, 5, or more nucleotides from the 5' end of the primer.

Similarly, one of ordinary skill in the art can select primers from the nucleotide sequence of SEQ ID NO:1 or SEQ ID NO:7 for selective amplification of preproTRH or Oct-T1 mRNA sequences, respectively. For example, exemplary primers specific for preproTRH include SEQ ID NO:9 and SEQ ID NO:10, which are derived from SEQ ID NO:1. Exemplary primers specific for Oct-T1 include SEQ ID NO:13 and SEQ ID NO:14, which are derived from SEQ ID NO:7. For amplification of tryptase-L, primers can be designed which are specific for each clone (i.e., which amplify a portion of either SEQ ID NO:3 or SEQ ID NO:5), or which amplify both clones (i.e., SEQ ID NO:3 and SEQ ID NO:5). As demonstrated in the Examples below, primer pairs specific to preproTRH, tryptase-L or Oct-T1 can be used to distinguish the expression of the genes in cells and tissues. Other exemplary primers can differ from the above by addition or deletion of 1, 2, 3, 4, 5, or more nucleotides from the 5' end of the primers above. One of ordinary skill in the art can determine with no more than routine experimentation the preferred primers for selective amplification of particular leukemia associated genes.

Additional methods which can distinguish nucleotide sequences of substantial homology, such as ligase chain reaction ("LCR") and other methods, will be apparent to skilled artisans.

As used herein with respect to nucleic acids, the term "isolated" means: (i) amplified in vitro by, for example, polymerase chain reaction (PCR); (ii) recombinantly produced by cloning; (iii) purified, as by cleavage and gel separation; or (iv) synthesized by, for example, chemical synthesis. An isolated nucleic acid is one which is readily manipulable by recombinant DNA techniques well known in the art. Thus, a nucleotide sequence contained in a vector in which 5' and 3' restriction sites are known or for which polymerase chain reaction (PCR) primer sequences have been disclosed is considered isolated but a nucleic acid sequence existing in its native state in its natural host is not. An isolated nucleic acid may be substantially purified, but need not be. For example, a nucleic acid that is isolated within a cloning or expression vector is not pure in that it may comprise only a tiny percentage of the material in the cell in which it resides. Such a nucleic acid is isolated, however, as the term is used herein because it is readily manipulable by standard techniques known to those of ordinary skill in the art.

The invention also provides isolated polypeptides which include unique fragments of SEQ ID NO:2, SEQ ID NO:4, SEQ ID NO:6 and SEQ ID NO:8. Such polypeptides are useful, for example, alone or as fusion proteins to generate antibodies, as a components of an immunoassay, or for determining the binding specificity of HLA molecules and/or CTL clones for preproTRH, tryptase-L and Oct-T1 proteins.

A unique fragment of a tryptase-L protein, for example, generally has the features and characteristics of unique fragments as discussed above in connection with nucleic acids. As will be recognized by those skilled in the art, the size of the unique fragment will depend upon factors such as whether the fragment constitutes a portion of a conserved protein domain. Thus, some regions of SEQ ID NO:4 (or SEQ ID NO:6), will require longer segments to be unique while others will require only short segments, typically between 5 and 12 amino acids (e.g. 5, 6, 7, 8, 9, 10, 11 and 12 amino acids long).

Unique fragments of a polypeptide preferably are those fragments which retain a distinct functional capability of the polypeptide. Functional capabilities which can be retained in a unique fragment of a polypeptide include interaction with antibodies, interaction with other polypeptides or fragments thereof, selective binding of nucleic acids, and enzymatic activity. A tumor rejection antigen is an example of a unique fragment of a tumor specific polypeptide which retains the functional capability of HLA binding and interaction with cytotoxic T lymphocytes. Tumor rejection antigens presented by HLA class I molecules typically are 9 amino acids in length, although peptides of 8, 9 and 10 and more amino acids also retain the capability to interact with HLA and cytotoxic T lymphocyte to an extent effective to provoke a cytotoxic T lymphocyte response (see, e.g., Van den Eynde & Brichard, Curr. Opin. Immunol. 7:674–681, 1995; Coulie et al., Stem Cells 13:393–403, 1995).

Those skilled in the art are well versed in methods for selecting unique amino acid sequences, typically on the basis of the ability of the unique fragment to selectively distinguish the sequence of interest from non-family members. A comparison of the sequence of the fragment to those on known data bases typically is all that is necessary.

The skilled artisan will also realize that conservative amino acid substitutions may be made in tryptase-L polypeptides to provide functionally active homologs of the foregoing polypeptides, i.e, the homologs retain the functional capabilities of the preproTRH, tryptase-L or Oct-T1 polypeptides. As used herein, a "conservative amino acid substitution" refers to an amino acid substitution which does not alter the relative charge or size characteristics of the protein in which the amino acid substitution is made. Conservative substitutions of amino acids include substitutions made amongst amino acids within the following groups: (a) M, I, L, V; (b) F, Y, W; (c) K, R, H; (d) A, G; (e) S, T; (f) Q, N; and (g) E, D.

Functionally equivalent variants of preproTRH, tryptase-L and/or Oct-T1 polypeptides, i.e., variants of polypeptides which retain the function of the natural polypeptides, can be prepared according to methods for altering polypeptide sequence known to one of ordinary skill in the art such as are found in references which compile such methods, e.g. *Molecular Cloning: A Laboratory Manual*, J. Sambrook, et al., eds., Second Edition, Cold Spring Harbor Laboratory Press, Cold Spring Harbor, N.Y., 1989, or *Current Protocols in Molecular Biology*, F. M. Ausubel, et al., eds., John Wiley & Sons, Inc., New York. For example, exemplary functionally equivalent variants of the tryptase-L polypeptides include conservative amino acid substitutions of SEQ ID NO:4 or and SEQ ID NO:6. Conservative amino-acid substitutions in the amino acid sequence of tryptase-L polypeptides to produce functionally equivalent variants of tryptase-L polypeptides typically are made by alteration of the nucleic acid encoding tryptase-L (SEQ ID NO:3, SEQ ID NO:5). Such substitutions can be made by a variety of methods known to one of ordinary skill in the art. For example, amino acid substitutions may be made by PCR-directed mutation, site-directed mutagenesis according to the method of Kunkel (Kunkel, *Proc. Nat. Acad. Sci. U.S.A.* 82: 488–492, 1985), or by chemical synthesis of a gene encoding a tryptase-L polypeptide. Where amino acid substitutions are made to a small unique fragment of a tryptase-L polypeptide, such as a 9 amino acid peptide, the substitutions can be made by directly synthesizing the peptide. The activity of functionally equivalent fragments of tryptase-L polypeptides can be tested by cloning the gene encoding the altered tryptase-L polypeptide into a bacterial or mammalian expression vector, introducing the vector into an appropriate host cell, expressing the altered tryptase-L polypeptide, and testing for a functional capability of the tryptase-L polypeptides as disclosed herein. Functionally equivalent variants of the preproTRH and Oct-T1 polypeptides can be prepared in a like manner.

As mentioned above, the invention embraces antisense oligonucleotides that selectively bind to a leukemia associated gene nucleic acid molecule, including those encoding a preproTRH protein, a tryptase-L protein or a Oct-T1 protein, to decrease transcription and/or translation of leukemia associated genes. This is desirable in virtually any medical condition wherein a reduction in leukemia associated gene product expression is desirable, including to reduce any aspect of a malignant hemopathy cell phenotype attributable to leukemia associated gene expression, such as expression of preproTRH, tryptase-L and/or Oct-T1. Antisense molecules, in this manner, can be used to slow down or arrest such aspects of a malignant leukemia cell phenotype as found in, inter alia, leukemia and solid forms such as lymphoma.

As used herein, the term "antisense oligonucleotide" or "antisense" describes an oligonucleotide that is an oligoribonucleotide, oligodeoxyribonucleotide, modified oligoribonucleotide, or modified oligodeoxyribonucleotide which hybridizes under physiological conditions to DNA comprising a particular gene or to an mRNA transcript of that gene and, thereby, inhibits the transcription of that gene and/or the translation of that mRNA. The antisense molecules are designed so as to interfere with transcription or translation of a target gene upon hybridization with the target gene. Those skilled in the art will recognize that the exact length of the antisense oligonucleotide and its degree of complementarity with its target will depend upon the specific target selected, including the sequence of the target and the particular bases which comprise that sequence. It is preferred that the antisense oligonucleotide be constructed and arranged so as to bind selectively with the target under physiological conditions, i.e., to hybridize substantially more to the target sequence than to any other sequence in the target cell under physiological conditions. Based upon SEQ ID NO:1, SEQ ID NO:3, SEQ ID NO:5 and/or SEQ ID NO:7, or upon allelic or homologous genomic and/or DNA sequences, one of skill in the art can easily choose and synthesize any of a number of appropriate antisense molecules for use in accordance with the present invention. In order to be sufficiently selective and potent for inhibition, such antisense oligonucleotides should comprise at least 7 (Wagner et al., *Nature Biotechnology* 14:840–844, 1996) and, more preferably, at least 15 consecutive bases which are complementary to the target. Most preferably, the antisense oligonucleotides comprise a complementary sequence of 20–30 bases. Although oligonucleotides may be chosen which are antisense to any region of the gene or mRNA transcripts, in preferred embodiments the antisense oligonucleotides correspond to N-terminal or 5' upstream sites such as translation initiation, transcription initiation or promoter sites. In addition, 3'-untranslated regions may be targeted. Targeting to mRNA splicing sites has also been used in the art but may be less preferred if alternative mRNA splicing occurs. In addition, the antisense is targeted, preferably, to sites in which mRNA secondary structure is not expected (see, e.g., Sainio et al., *Cell Mol. Neurobiol.* 14(5):439–457, 1994) and at which proteins are not expected to bind. Finally, although, SEQ ID NOs:1, 3, 5 and 7 disclose cDNA sequences, one of ordinary skill in the art may easily derive the genomic DNA corresponding to the cDNAs of SEQ ID NOs:1, 3, 5 and 7. Thus, the present invention also provides for antisense oligonucleotides which are complementary to the genomic DNA corresponding to SEQ ID NOs:1, 3, 5 and 7. Similarly, antisense to allelic or homologous DNAs and genomic DNAs are enabled without undue experimentation.

In one set of embodiments, the antisense oligonucleotides of the invention may be composed of "natural" deoxyribonucleotides, ribonucleotides, or any combination thereof. That is, the 5' end of one native nucleotide and the 3' end of another native nucleotide may be covalently linked, as in natural systems, via a phosphodiester internucleoside linkage. These oligonucleotides may be prepared by art recognized methods which may be carried out manually or by an automated synthesizer. They also may be produced recombinantly by vectors.

In preferred embodiments, however, the antisense oligonucleotides of the invention also may include "modified" oligonucleotides. That is, the oligonucleotides may be modified in a number of ways which do not prevent them from hybridizing to their target but which enhance their stability or targeting or which otherwise enhance their therapeutic effectiveness.

The term "modified oligonucleotide" as used herein describes an oligonucleotide in which (1) at least two of its nucleotides are covalently linked via a synthetic internucleoside linkage (i.e., a linkage other than a phosphodiester linkage between the 5' end of one nucleotide and the 3' end of another nucleotide) and/or (2) a chemical group not normally associated with nucleic acids has been covalently attached to the oligonucleotide. Preferred synthetic intemucleoside linkages are phosphorothioates, alkylphosphonates, phosphorodithioates, is phosphate esters, alkylphosphonothioates, phosphoramidates, carbamates, carbonates, phosphate triesters, acetamidates, peptides, and carboxymethyl esters.

The term "modified oligonucleotide" also encompasses oligonucleotides with a covalently modified base and/or sugar. For example, modified oligonucleotides include oligonucleotides having backbone sugars which are covalently attached to low molecular weight organic groups other than a hydroxyl group at the 3' position and other than a phosphate group at the 5' position. Thus modified oligonucleotides may include a 2'-O-alkylated ribose group. In addition, modified oligonucleotides may include sugars such as arabinose instead of ribose. Modified oligonucleotides also can include base analogs such as C-5 propyne modified bases (Wagner et al., *Nature Biotechnology* 14:840–844, 1996). The present invention, thus, contemplates pharmaceutical preparations containing modified antisense molecules that are complementary to and hybridizable with, under physiological conditions, nucleic acids encoding leukemia associated proteins, together with pharmaceutically acceptable carriers.

It will also be recognized from the examples that the invention embraces the use of the preproTRH, tryptase-L and Oct-T1 sequences in expression vectors, as well as to transfect host cells and cell lines, be these prokaryotic (e.g., *E. coli*), or eukaryotic (e.g., CHO cells, COS cells, yeast expression systems and recombinant baculovirus expression in insect cells). Especially useful are mammalian cells such as mouse, hamster, pig, goat, primate, etc. They can be of a wide variety of tissue types, including mast cells, fibroblasts, oocytes and lymphocytes, and they may be primary cells or cell lines. Specific examples include dendritic cells, U293 cells, peripheral blood leukocytes, bone marrow stem cells and embryonic stem cells. The expression vectors require that the pertinent sequence, i.e., those nucleic acids described supra, be operably linked to a promoter. In instances in which a human HLA class I molecule presents tumor rejection antigens derived from the preproTRH, tryptase-L and Oct-T1 genes, the expression vector may also include a nucleic acid sequence coding for the HLA molecule that presents any particular tumor rejection antigen derived from these genes and polypeptides. Alternatively, the nucleic acid sequence coding for such a HLA molecule can be contained within a separate expression vector. In a situation where the vector contains both coding sequences, the single vector can be used to transfect a cell which does not normally express either one. Where the coding sequences for the tumor rejection antigen precursor and the HLA molecule which presents it are contained on separate expression vectors, the expression vectors can be cotransfected. The tumor rejection antigen precursor coding sequence may be used alone, when, e.g. the host cell already expresses a HLA molecule which presents a TRA derived from preproTRH, tryptase-L and/or Oct-T1 TRAPs. Of course, there is no limit on the particular host cell which can be used. As the vectors which contain the two coding sequences may be used in any antigen-presenting cells if desired, and the gene for tumor rejection antigen precursor can be used in host cells which do not express a HLA molecule which presents a preproTRH, tryptase-L and/or Oct-T1 TRA. Further, cell-free transcription systems may be used in lieu of cells.

As used herein, a "vector" may be any of a number of nucleic acids into which a desired sequence may be inserted by restriction and ligation for transport between different genetic environments or for expression in a host cell. Vectors are typically composed of DNA although RNA vectors are also available. Vectors include, but are not limited to, plasmids and phagemids. A cloning vector is one which is able to replicate in a host cell, and which is further characterized by one or more endonuclease restriction sites at which the vector may be cut in a determinable fashion and into which a desired DNA sequence may be ligated such that the new recombinant vector retains its ability to replicate in the host cell. In the case of plasmids, replication of the desired sequence may occur many times as the plasmid increases in copy number within the host bacterium or just a single time per host before the host reproduces by mitosis. In the case of phage, replication may occur actively during a lytic phase or passively during a lysogenic phase. An expression vector is one into which a desired DNA sequence may be inserted by restriction and ligation such that it is operably joined to regulatory sequences and may be expressed as an RNA transcript. Vectors may further contain one or more marker sequences suitable for use in the identification of cells which have or have not been transformed or transfected with the vector. Markers include, for example, genes encoding proteins which increase or decrease either resistance or sensitivity to antibiotics or other compounds, genes which encode enzymes whose activities are detectable by standard assays known in the art (e.g. β-galactosidase or alkaline phosphatase), and genes which visibly affect the phenotype of transformed or transfected cells, hosts, colonies or plaques. Preferred vectors are those capable of autonomous replication and expression of the structural gene products present in the DNA segments to which they are operably joined.

As used herein, a coding sequence and regulatory sequences are said to be "operably" joined when they are covalently linked in such a way as to place the expression or transcription of the coding sequence under the influence or control of the regulatory sequences. If it is desired that the coding sequences be translated into a functional protein, two DNA sequences are said to be operably joined if induction of a promoter in the 5' regulatory sequences results in the transcription of the coding sequence and if the nature of the linkage between the two DNA sequences does not (1) result in the introduction of a frame-shift mutation, (2) interfere with the ability of the promoter region to direct the transcription of the coding sequences, or (3) interfere with the ability of the corresponding RNA transcript to be translated into a protein. Thus, a promoter region would be operably joined to a coding sequence if the promoter region were capable of effecting transcription of that DNA sequence such that the resulting transcript might be translated into the desired protein or polypeptide.

The precise nature of the regulatory sequences needed for gene expression may vary between species or cell types, but shall in general include, as necessary, 5' non-transcribing and 5' non-translating sequences involved with the initiation of transcription and translation respectively, such as a TAT box, capping sequence, CAAT sequence, and the like. Especially, such 5' non-transcribing regulatory sequences will include a promoter region which includes a promoter sequence for transcriptional control of the operably joined gene. Regulatory sequences may also include enhancer sequences or upstream activator sequences as desired. The vectors of the invention may optionally include 5' leader or signal sequences, 5' or 3'. The choice and design of an appropriate vector is within the ability and discretion of one of ordinary skill in the art.

Expression vectors containing all the necessary elements for expression are commercially available and known to those skilled in the art. See *Molecular Cloning: A Laboratory Manual*, J. Sambrook, et al., eds., Second Edition, Cold Spring Harbor Laboratory Press, Cold Spring Harbor, N.Y., 1989. Cells are genetically engineered by the introduction into the cells of heterologous DNA (RNA) encoding the preproTRH, tryptase-L or Oct-T1 tumor specific polypeptide or fragment or variant thereof. That heterologous DNA (RNA) is placed under operable control of transcriptional elements to permit the expression of the heterologous DNA in the host cell.

Preferred systems for mRNA expression in mammalian cells are those such as pRc/CMV (available from Invitrogen, Carlsbad, Calif.) that contain a selectable marker such as a gene that confers G418 resistance (which facilitates the selection of stably transfected cell lines) and the human cytomegalovirus (CMV) enhancer-promoter sequences. Additionally, suitable for expression in primate or canine cell lines is the pCEP4 vector (Invitrogen), which contains an Epstein Barr virus (EBV) origin of replication, facilitating the maintenance of plasmid as a multicopy extrachromosomal element. Another expression vector is the pEF-BOS plasmid containing the promoter of polypeptide Elongation Factor 1α, which stimulates efficiently transcription in vitro. The plasmid is described by Mishizuma and Nagata (*Nuc. Acids Res.* 18:5322, 1990), and its use in transfection experiments is disclosed by, for example, Demoulin (*Mol. Cell. Biol.* 16:4710–4716, 1996). Still another preferred expression vector is an adenovirus, described by Stratford-Perricaudet, which is defective for E1 and E3 proteins (*J. Clin. Invest.* 90:626–630, 1992). The use of the adenovirus as an Adeno.P1A recombinant is disclosed by Warnier et al., in intradermal injection in mice for immunization against P1A (*Int. J. Cancer.* 67:303–310, 1996).

The invention also embraces so-called expression kits, which allow the artisan to prepare a desired expression vector or vectors. Such expression kits include at least separate portions of each of the previously discussed coding sequences. Other components may be added, as desired, as long as the previously mentioned sequences, which are required, are included.

The invention also involves agents which bind to leukemia associated polypeptides including preproTRH, tryptase-L and Oct-T1, and in certain embodiments preferably to unique fragments of the preproTRH, tryptase-L and Oct-T1 polypeptides. Such binding partners can be used in screening assays to detect the presence or absence of a preproTRH, tryptase-L or Oct-T1 polypeptide and in purification protocols to isolate preproTRH, tryptase-L or Oct-T1 polypeptides. Likewise, such binding partners can be used to selectively target drugs, toxins or other molecules to leukemia cells which present preproTRH, tryptase-L or Oct-T1 leukemia associated polypeptides. In this manner, cells present in solid or non-solid tumors which express preproTRH, tryptase-L or Oct-T1 leukemia associated polypeptides can be treated with cytotoxic compounds.

The invention, therefore, involves antibodies or fragments of antibodies having the ability to selectively bind to preproTRH, tryptase-L or Oct-T1 leukemia associated polypeptides, and preferably to unique fragments thereof. Antibodies include polyclonal and monoclonal antibodies, prepared according to conventional methodology.

The antibodies of the present invention thus are prepared by any of a variety of methods, including administering protein, fragments of protein, cells expressing the protein or fragments thereof and the like to an animal to induce polyclonal antibodies. The production of monoclonal antibodies is according to techniques well known in the art. As detailed herein, such antibodies may be used for example to identify tissues expressing protein or to purify protein. Antibodies also may be coupled to specific labeling agents for imaging or to antitumor agents, including, but not limited to, methotrexate, radioiodinated compounds, toxins such as ricin, other cytostatic or cytolytic drugs, and so forth. Antibodies prepared according to the invention also preferably are specific for the TRA/HLA complexes described herein.

Significantly, as is well-known in the art, only a small portion of an antibody molecule, the paratope, is involved in the binding of the antibody to its epitope (see, in general, Clark, W. R. (1986) *The Experimental Foundations of Modern Immunology* Wiley & Sons, Inc., New York; Roitt, I. (1991) *Essential Immunology*, 7th Ed., Blackwell Scientific Publications, Oxford). The pFc' and Fc regions, for example, are effectors of the complement cascade but are not involved in antigen binding. An antibody from which the pFc' region has been enzymatically cleaved, or which has been produced without the pFc' region, designated an F(ab')$_2$ fragment, retains both of the antigen binding sites of an intact antibody. Similarly, an antibody from which the Fc region has been enzymatically cleaved, or which has been produced without the Fc region, designated an Fab fragment, retains one of the antigen binding sites of an intact antibody molecule. Proceeding further, Fab fragments consist of a covalently bound antibody light chain and a portion of the antibody heavy chain denoted Fd. The Fd fragments are the major determinant of antibody specificity (a single Fd fragment may be associated with up to ten different light chains without altering antibody specificity) and Fd fragments retain epitope-binding ability in isolation.

Within the antigen-binding portion of an antibody, as is well-known in the art, there are complementarity determining regions (CDRs), which directly interact with the epitope of the antigen, and framework regions (FRs), which maintain the tertiary structure of the paratope (see, in general, Clark, 1986; Roitt, 1991). In both the heavy chain Fd fragment and the light chain of IgG immunoglobulins, there are four framework regions (FR1 through FR4) separated respectively by three complementarity determining regions (CDR1 through CDR3). The CDRs, and in particular the CDR3 regions, and more particularly the heavy chain CDR3, are largely responsible for antibody specificity.

It is now well-established in the art that the non-CDR regions of a mammalian antibody may be replaced with similar regions of conspecific or heterospecific antibodies while retaining the epitopic specificity of the original antibody. This is most clearly manifested in the development and use of "humanized" antibodies in which non-human CDRs are covalently joined to human FR and/or Fc/pFc' regions to produce a functional antibody. Thus, for example, PCT International Publication Number WO 92/04381 teaches the production and use of humanized murine RSV antibodies in which at least a portion of the murine FR regions have been replaced by FR regions of human origin. Such antibodies, including fragments of intact antibodies with antigen-binding ability, are often referred to as "chimeric" antibodies.

Thus, as will be apparent to one of ordinary skill in the art, the present invention also provides for F(ab')$_2$, Fab, Fv and Fd fragments; chimeric antibodies in which the Fc and/or FR and/or CDR1 and/or CDR2 and/or light chain CDR3 regions have been replaced by homologous human or non-human sequences; chimeric F(ab')$_2$ fragment antibodies in which the FR and/or CDR1 and/or CDR2 and/or light chain CDR3 regions have been replaced by homologous human or non-human sequences; chimeric Fab fragment antibodies in which the FR and/or CDR1 and/or CDR2 and/or light chain CDR3 regions have been replaced by homologous human or non-human sequences; and chimeric Fd fragment antibodies in which the FR and/or CDR1 and/or CDR2 regions have been replaced by homologous human or non-human sequences. The present invention also includes so-called single chain antibodies. Thus, the invention involves polypeptides of numerous size and type that bind specifically to leukemia associated polypeptides including preproTRH, tryptase-L or Oct-T1. These polypeptides may be derived also from sources other than antibody technology. For example, such polypeptide binding agents can be provided by degenerate peptide libraries which can be readily prepared in solution, in immobilized form or as phage display libraries. Combinatorial libraries also can be synthesized of peptides containing one or more amino acids. Libraries further can be synthesized of peptoids and non-peptide synthetic moieties.

Phage display can be particularly effective in identifying binding peptides useful according to the invention. Briefly, one prepares a phage library (using e.g. m13, fd, or lambda phage), displaying inserts from 4 to about 80 amino acid residues using conventional procedures. The inserts may represent a completely degenerate or biased array. One then can select phage-bearing inserts which bind to a preproTRH, tryptase-L or Oct-T1 leukemia associated polypeptide. This process can be repeated through several cycles of reselection of phage that bind to a preproTRH, tryptase-L or Oct-T1 polypeptide. Repeated rounds lead to enrichment of phage bearing particular sequences. DNA sequence analysis can be conducted to identify the sequences of the expressed polypeptides. The minimal linear portion of the sequence that binds to the preproTRH, tryptase-L or Oct-T1 polypeptide can be determined. One can repeat the procedure using a biased library containing inserts containing part or all of the minimal linear portion plus one or more additional degenerate residues upstream or downstream thereof. Thus, the leukemia associated polypeptides of the invention can be used to screen peptide libraries, including phage display libraries, to identify and select peptide binding partners of the leukemia associated polypeptides of the invention. Such molecules can be used, as described, for screening assays, for diagnostic assays, for purification protocols or for targeting drugs, toxins and/or labeling agents (e.g. radioisotopes, fluorescent molecules, etc.) to cells which express leukemia associated genes such as those leukemia cells which present preproTRH, tryptase-L or Oct-T1 polypeptides on the cell surface. Such binding agent molecules can also be prepared to bind complexes of an preproTRH, tryptase-L or Oct-T1 polypeptide and an HLA molecule by selecting the binding agent using such complexes. Drug molecules that would disable or destroy leukemia cells which express such complexes or preproTRH, tryptase-L or Oct-T1 polypeptides are known to those skilled in the art and are commercially available. For example, the immunotoxin art provides examples of toxins which are effective when delivered to a cell by an antibody or fragment thereof. Examples of toxins include ribosome-damaging toxins derived from plants or bacterial such as ricin, abrin, saporin, Pseudomonas endotoxin, diphtheria toxin, A chain toxins, blocked ricin, etc.

The skilled artisan can determine which HLA molecule binds to tumor rejection antigens derived from preproTRH, tryptase-L and/or Oct-T1 tumor rejection antigen precursors by, e.g., experiments utilizing antibodies to block specifically individual HLA class I molecules. For example, antibodies which bind selectively to HLA-A2 will prevent efficient presentation of TRAs specifically presented by HLA-A2. Thus, if TRAs derived from leukemia associated genes such as preproTRH, tryptase-L and/or Oct-T1 are presented by HLA-A2, then the inclusion of anti-HLA-A2 antibodies in an in vitro assay will block the presentation of these TRAs. An assay for determining the nature of the HLA molecule is found in U.S. patent application Ser. No. 08/530, 569. Briefly, in determining the HLA molecule type, inhibition experiments were carried out where the production of tumor necrosis factor (TNF) by cytotoxic T lymphocyte (CTL) clone 263/17 was tested in the presence of monoclonal antibodies directed against HLA molecules or against CD4/CD8 accessory molecules. Four monoclonal antibodies were found to inhibit the production of TNF by CTL 263/17: monoclonal antibody W6/32, which is directed against all HLA class I molecules (Parham et al., *J. Immunol.* 123:342, 1979), antibody B1.23.2 which recognizes HLA-B and C molecules (Rebai et al., *Tissue Antigens* 22:107, 1983), antibody ME-1 which specifically recognizes HLA-B7 (Ellis et al., *Hum. Immunol.* 5:49, 1982) and antibody B9.4.1 against CD8. No inhibition was found with antibodies directed against HLA Class II DR molecules (L243: Lampson et al., *J. Immunol.* 125:293, 1980), against HLA-A3 (GAPA 3: Berger et al., *Hybridoma* 1:87, 1982) or against CD4 (13B.8.82). The conclusion was that CTL 263/17 was of the CD8 type, and recognized an antigen presented by HLA-B7. Similar experiments using widely available anti-HLA antibodies can be performed to determine the nature of a HLA molecule.

The invention as described herein has a number of uses, some of which are described herein. First, the invention permits the artisan to diagnose a disorder characterized by expression of the TRAP. These methods involve determining expression of the TRAP gene, and/or TRAs derived therefrom, such as a TRA presented by HLA-A2, HLA-A26, HLA-B7, etc. In the former situation, such determinations can be carried out via any standard nucleic acid determination assay, including the polymerase chain reaction, or assaying with labeled hybridization probes. In the latter situation, assaying with binding partners for complexes of TRA and HLA, such as antibodies, is especially preferred. An alternate method for determination is a TNF release assay, of the type described supra.

The isolation of the TRAP gene also makes it possible to isolate the TRAP molecule tself, especially TRAP molecules containing the acmcnino acid sequences coded for by SEQ ID NO:2, SEQ ID NO:4, SEQ ID NO:6 or SEQ ID NO:8. Other TRAPs or TRAs encoded by leukemia associated genes and recognized by other CTL clones and/or presented by other HLA molecules may be isolated by the procedures detailed herein. (There are numerous HLA molecules known to those skilled in the art, including but not limited to, those encoded by HLA-A, HLA-B, HLA-C, HLA-E, HLA-F and HLA-G genes.) A variety of methodologies well-known to the skilled practitioner can be utilized to obtain isolated TRAP molecules. The protein may be purified from cells which naturally produce the protein. Alternatively, an expression vector may be introduced into cells to cause production of the protein. In another method, mRNA transcripts may be microinjected or otherwise introduced into cells to cause production of the encoded protein. Translation of mRNA in cell-free extracts such as the reticulocyte lysate system also may be used to produce protein. Peptides comprising TRAs of the invention may also be synthesized in vitro. Those skilled in the art also can readily follow known methods for isolating proteins in order to obtain isolated TRAPs and/or TRAs derived therefrom. These include, but are not limited to, immunochromotography, HPLC, size-exclusion chromatography, ion-exchange chromatography and immune-affinity chromatography.

These isolated molecules when processed and presented as the TRA, or as complexes of TRA and HLA, such as HLA-A2, HLA-A26 or HLA-B7, etc. may be combined with materials such as adjuvants to produce vaccines useful in treating disorders characterized by expression of the TRAP molecule. In addition, vaccines can be prepared from cells which present the TRA/HLA complexes on their surface, such as non-proliferative cancer cells, non-proliferative transfectants, etcetera. In all cases where cells are used as a vaccine, these can be cells transfected with coding sequences for one or both of the components necessary to provoke a CTL response, or be cells which already express both molecules without the need for transfection. Vaccines also encompass naked DNA or RNA, encoding a leukemia associated TRA or precursor thereof, which may be produced in vitro and administered via injection, particle bombardment, nasal aspiration and other methods. Vaccines of the "naked nucleic acid" type have been demonstrated to provoke an immunological response including generation of CTLs specific for the peptide encoded by the naked nucleic acid (*Science* 259:1745–1748, 1993). When "disorder" is used herein, it refers to any pathological condition where the tumor rejection antigen precursor is expressed. An example of such a disorder is cancer, leukemias and lymphomas in particular.

In addition, vaccines can be prepared from cells which present the TRA/HLA complexes on their surface, such as non-proliferative cancer cells, non-proliferative transfectants, etcetera. In all cases where cells are used as a vaccine, these can be cells transfected with coding sequences for one or both of the components necessary to provoke a CTL response, or be cells which already express both molecules without the need for transfection.

Therapeutic approaches based upon the disclosure are premised on a response by a subject's immune system, leading to lysis of TRA presenting cells, such as HLA-B7 cells. One such approach is the administration of autologous CTLs specific to the complex to a subject with abnormal cells of the phenotype at issue. It is within the skill of the artisan to develop such CTLs in vitro. Generally, a sample of cells taken from a subject, such as blood cells, are contacted with a cell presenting the complex and capable of provoking CTLs to proliferate. The target cell can be a transfectant, such as a COS cell of the type described supra. These transfectants present the desired complex of their surface and, when combined with a CTL of interest, stimulate its proliferation. COS cells, such as those used herein are widely available, as are other suitable host cells. Specific production of a CTL is well known to one of ordinary skill in the art. The clonally expanded autologous CTLs then are administered to the subject. Other CTLs specific to preproTRH, tryptase-L and/or Oct-T1 may be isolated and administered by similar methods.

To detail a therapeutic methodology, referred to as adoptive transfer (Greenberg, *J. Immunol.* 136(5): 1917, 1986; Riddel et al., *Science* 257: 238, 1992; Lynch et al, *Eur. J. Immunol.* 21: 1403–1410, 1991; Kast et al., *Cell* 59: 603–614, 1989), cells presenting the desired complex are combined with CTLs leading to proliferation of the CTLs specific thereto. The proliferated CTLs are then administered to a subject with a cellular abnormality which is characterized by certain of the abnormal cells presenting the particular complex. The CTLs then lyse the abnormal cells, thereby achieving the desired therapeutic goal.

The foregoing therapy assumes that at least some of the subject's abnormal cells present the relevant HLA/TRA complex. This can be determined very easily, as the art is very familiar with methods for identifying cells which present a particular HLA molecule, as well as how to identify cells expressing DNA of the pertinent sequences, in this case a leukemia associated gene sequence. Once cells presenting the relevant complex are identified via the foregoing screening methodology, they can be combined with a sample from a patient, where the sample contains CTLs. If the complex presenting cells are lysed by the mixed CTL sample, then it can be assumed that a leukemia associated gene derived TRA is being presented, and the subject is an appropriate candidate for the therapeutic approaches set forth supra.

Adoptive transfer is not the only form of therapy that is available in accordance with the invention. CTLs can also be provoked in vivo, using a number of approaches. One approach is the use of non-proliferative cells expressing the complex. The cells used in this approach may be those that normally express the complex, such as irradiated tumor cells or cells transfected with one or both of the genes necessary for presentation of the complex. Chen et al., *Proc. Natl. Acad. Sci. USA* 88: 110–114 (1991) exemplifies this approach, showing the use of transfected cells expressing HPV E7 peptides in a therapeutic regime. Various cell types may be used. Similarly, vectors carrying one or both of the genes of interest may be used. Viral or bacterial vectors are especially preferred. For example, nucleic acids which encode a preproTRH, tryptase-L or Oct-T1 TRA may be operably linked to promoter and enhancer sequences which direct expression of the preproTRH, tryptase-L or Oct-T1 TRA in certain tissues or cell types. The nucleic acid may be incorporated into an expression vector. Expression vectors may be unmodified extrachromosomal nucleic acids, plasmids or viral genomes constructed or modified to enable insertion of exogenous nucleic acids, such as those encoding preproTRH, tryptase-L or Oct-T1 TRAs. Nucleic acids encoding a preproTRH, tryptase-L or Oct-T1 TRA also may be inserted into a retroviral genome, thereby facilitating integration of the nucleic acid into the genome of the target tissue or cell type. In these systems, the gene of interest is carried by a microorganism, e.g., a Vaccinia virus, retrovirus or the bacteria BCG, and the materials defacto "infect" host cells. The cells which result present the complex of interest, and are recognized by autologous CTLs, which then proliferate.

A similar effect can be achieved by combining a TRAP or a stimulatory fragment thereof with an adjuvant to facilitate incorporation into HLA presenting cells in vivo. The TRAP is processed to yield the peptide partner of the HLA molecule while the TRA is presented without the need for further processing. Generally, subjects can receive an intradermal injection of an effective amount of a preproTRH, tryptase-L and/or Oct-T1 encoded TRAP, and/or TRAs derived therefrom. Initial doses can be followed by booster doses, following immunization protocols standard in the art.

As part of the immunization protocols, substances which potentiate the immune response may be administered with nucleic acid or peptide components of a cancer vaccine. Such immune response potentiating compound may be classified as either adjuvants or cytokines. Adjuvants may enhance the immunological response by providing a reservoir of antigen (extracellularly or within macrophages), activating macrophages and stimulating specific sets of lymphocytes. Adjuvants of many kinds are well known in the art; specific examples include MPL (SmithKline Beecham), a congener obtained after purification and acid hydrolysis of *Salmonella Minnesota* Re 595 lipopolysaccharide, QS21 (SmithKline Beecham), a pure QA-21 saponin purified from *Quillja saponaria* extract, and various water-in-oil emulsions prepared from biodegradable oils such as squalene and/or tocopherol. Cytokines are also useful in vaccination protocols as a result of lymphocyte stimulatory properties. Many cytokines useful for such purposes will be known to one of ordinary skill in the art, including interleukin-12 (IL-12) which has been shown to enhance the protective effects of vaccines (*Science* 268: 1432–1434, 1995).

When administered, the therapeutic compositions of the present invention are administered in pharmaceutically acceptable preparations. Such preparations may routinely contain pharmaceutically acceptable concentrations of salt, buffering agents, preservatives, compatible carriers, supplementary immune potentiating agents such as adjuvants and cytokines and optionally other therapeutic agents.

The term "pharmaceutically acceptable" means a non-toxic material that does not interfere with the effectiveness of the biological activity of the active ingredients. The term "physiologically acceptable" refers to a non-toxic material that is compatible with a biological system such as a cell, cell culture, tissue, or organism. The characteristics of the carrier will depend on the route of administration. Physiologically and pharmaceutically acceptable carriers include diluents, fillers, salts, buffers, stabilizers, solubilizers, and other materials which are well known in the art.

The therapeutics of the invention can be administered by any conventional route, including injection or by gradual infusion over time. The administration may, for example, be oral, intravenous, intraperitoneal, intramuscular, intracavity, subcutaneous, or transdermal. When antibodies are used therapeutically, a preferred route of administration is by pulmonary aerosol. Techniques for preparing aerosol delivery systems containing antibodies are well known to those of skill in the art. Generally, such systems should utilize components which will not significantly impair the biological properties of the antibodies, such as the paratope binding capacity (see, for example, Sciarra and Cutie, "Aerosols," in *Remington's Pharmaceutical Sciences*, 18th edition, 1990, pp 1694–1712). Those of skill in the art can readily determine the various parameters and conditions for producing antibody aerosols without resort to undue experimentation. When using antisense preparations of the invention, slow intravenous administration is preferred.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

The invention also contemplates gene therapy. The procedure for performing ex vivo gene therapy is outlined in U.S. Pat. No. 5,399,346 and in exhibits submitted in the file history of that patent, all of which are publicly available documents. In general, it involves introduction in vitro of a functional copy of a gene into a cell(s) of a subject which contains a defective copy of the gene, and returning the genetically engineered cell(s) to the subject. The functional copy of the gene is under operable control of regulatory elements which permit expression of the gene in the genetically engineered cell(s). Numerous transfection and transduction techniques as well as appropriate expression vectors are well known to those of ordinary skill in the art, some of which are described in PCT application WO95/00654. In vivo gene therapy using vectors such as adenovirus also is contemplated according to the invention.

The preparations of the invention are administered in effective amounts. An effective amount is that amount of a pharmaceutical preparation that alone, or together with further doses, stimulates the desired response. In the case of treating cancer, the desired response is inhibiting the progression of the cancer. This may involve only slowing the progression of the disease temporarily, although more preferably, it involves halting the progression of the disease permanently. This can be monitored by routine methods or can be monitored according to diagnostic methods of the invention discussed herein.

Where it is desired to stimulate an immune response using a therapeutic composition of the invention, this may involve the stimulation of a humoral antibody response resulting in an increase in antibody titer in serum, a clonal expansion of cytotoxic lymphocytes, or some other desirable immunologic response. It is believed that doses of immunogens ranging from one nanogram/kilogram to 100 milligrams/kilogram, depending upon the mode of administration, would be effective. The preferred range is believed to be between 500 nanograms and 500 micrograms per kilogram. The absolute amount will depend upon a variety of factors, including the material selected for administration, whether the administration is in single or multiple doses, and individual patient parameters including age, physical condition, size, weight, and the stage of the disease. These factors are well known to those of ordinary skill in the art and can be addressed with no more than routine experimentation.

EXAMPLES

Example 1

Representational Difference Analysis—Subtractive cDNA hybridizations between leukemia and normal leukoccytes.

1. Procedure

Tester population: PBL from a female patient (SIAX, LB-1079) with newly diagnosed acute myelogenous leukemia (FAB-M2 subtype), with a chromosomal rearrangement t(8;21)(q22;q22) detected by cytogenetic analysis. The PBL were collected by leukapheresis before starting chemotherapy (approximately 70% of the PBL were leukemia blast cells), purified on a Lymphoprep (Ficoll) gradient, washed and frozen in culture medium and DMSO at −80° C. For RNA preparation, $6 \times 10^8$ cells were thawed, washed and centrifuged as a dry cell pellet, containing $4.6 \times 10^8$ cells.

Driver population: PBL from a normal person were collected by leukapheresis, they were purified on a Lymphoprep (Ficoll) gradient, washed and frozen at −80° C. as a dry cell pellet after centrifugation, containing $5 \times 10^8$ cells.

Total RNA preparation: The guanidinium isothiocyanate/cesium chloride procedure was used [L. G. Davis, M. D. Dibner, J. F. Battey, *Basic Methods in Molecular Biology*, Elsevier, N.Y., 1986, p. 130–135]. 390 μg and 50 μg were obtained from tester and driver populations respectively.

mRNA purification: Oligo-dT columns (Pharmacia mRNA Purification Kit, Pharmacia, Uppsala, Sweden) were used according to the manufacturer's protocol.

cDNA preparation: cDNA was prepared according to the manufacturer's protocol (Amersham, cDNA Synthesis Module). 6 μg and 2 μg were obtained from tester and driver populations respectively.

Difference analysis: The cDNA Difference Analysis Protocol of Hubank and Schatz (Nucleic Acids Res. 22: 5640–5648, 1994) was followed for the preparation of tester representation (TR), driver representation (DR), difference product 1 and difference product 2. Some particularities concerning the preparation of tester representation must be mentioned: 1) only 600 ng (and not 1.2 μg have been used in the initial ligation of adaptors; 2) the PCR reaction has been divided in 40 aliquots. Some particularities concerning the preparation of difference product 1 (DP1) must be mentioned: only 0.2 μg TR and 20 μg DR (and not 0.4 and 40 μg) were used in 5 μl hybridization buffer. Some particularities concerning the preparation of difference product 2 (DP2) must be mentioned: only 2.5 ng TR and 20 μg DR (and not 50 ng and 40 μg) were used in 5 μl hybridization buffer. Finally, no third difference product could be obtained.

Cloning of the tester representation and difference products 1 and 2: The cDNAs of the tester representation and difference products 1 and 2 obtained after digestion with DpnII were cloned by common ligation into the BamHI cloning site of vector pTZ18R, digested with BamHI (DpnII and BamHI cohesive ends are mutually compatible) and dephosphorylated with Calf Intestinal Phosphatase. The ligation products were used to transform competent Top10F' bacteria by electroporation. Transformed bacteria were selected on agar plates with ampicillin, their plasmid DNA was purified by miniprep DNA extraction (Qiaprep, Qiagen), and analyzed by BamHI digestion and DNA sequencing.

2. Results

Sequencing of 16 clones with DP2 products: Some clones contained more than 1 insert. Note also that 1 single mRNA can provide more than one amplified DpnII restriction fragment. Because two thirds of the individual inserts were derived from the myeloperoxidase (MPO) mRNA, more bacterial colonies were isolated after hybridization with a myeloperoxydase-specific oligonucleotide probe. 48 MPO-negative colonies were selected and grown with ampicillin, their plasmid DNA was purified by miniprep DNA extraction (Qiaprep, Qiagen), and analysed by DNA sequencing.

Conclusions: The majority of cDNA fragments amplified by the RDA method, using leukemia cells as tester population, and normal PBL as driver population, derived from the myeloperoxidase mRNA. The MPO gene is highly expressed in normal and leukemic myeloid progenitor cells, but not in differentiated white blood cells. This is the reason why derived cDNA fragments are amplified by RDA. This also explains the presence of CD34 which was also amplified by RDA when normal PBL are used as the driver population. The presence of cDNA fragments derived from highly expressed ubiquitous RNAs (28S and 40S ribosomal RNA genes) probably results from a residual background after two cycles of differential hybridization. Some cDNA fragments are derived from known genes.

For the last two categories, we have designed specific PCR primer pairs, derived from the sequence obtained from the cloned fragments. RT-PCR was performed on a few leukemia, normal PBL and normal bone marrow samples. The genes expressed only in leukemia samples were further tested for their expression on a larger panel of normal and leukemic tissues. Only three genes appear to show a leukemia-specific expression pattern:

The prepro TRH gene.

The gene encoding an mRNA with strong (but not complete) homology with the five known tryptase genes. This gene will be further referred to as tryptase-L (L for leukemia).

An apparently new gene, further referred to as SIAX DP2-64.

The cDNAs of these three genes have been cloned from a cDNA library obtained from the same leukemia (SIAX, LB-1079), and sequenced. We have tested their expression by RT-PCR on normal tissue, leukemia and solid tumor samples. These data are further detailed in the following pages.

Example 2

Pre-pro-thyrotropin-releasing hormone gene (preproTRH)

Cloning the cDNA: The cDNA library NVB32 was prepared as follows: Total RNA was extracted from the thawed leukemic PBL obtained from patient SIAX, LB-1079 (see tester population, RDA protocol, Example 1). Poly-A RNA was purified on oligo-dT columns (Pharmacia mRNA Purification Kit), according to the manufacturer's protocol. cDNA was prepared with Superscript kit (Gibco-BRL), according to the manufacturer's protocol, with random primers. The cDNA fragments were ligated to the EcoRI adaptors, fractionated on a chromatography column (4 fractions: A, B, C, and D were obtained) and ligated into the EcoRI digested and dephosphorylated pcDSRalpha vector. The ligation products were used to transform Top10F' competent bacteria by electroporation. Transformed bacteria colonies were obtained after selective growth with ampicillin, pooled with respect to fraction, and kept frozen at −80° C. Fraction B appeared to have the largest inserts.

The B fraction of the NVB329 cDNA library was screened for preproTRH clones by hybridizing 12,000 colonies with a $^{32}$P-labelled PCR probe amplified from SIAX cDNA. Sixteen colonies were found to be positive, with two of them containing a plasmid with a ~1.6 kb insert, corresponding to the predicted mRNA size. Only one of both recombinant plasmids (clone CHM327-3A/8) had its insert oriented in the right direction.

2. Sequencing: Clone CHM327-3A/8 has been fully sequenced (SEQ ID NO:1; see FIG. 1), using the Delta-Taq Sequencing Kit (Amersham). Its sequence is completely identical to the published sequence of preproTRH, except for the presence of an additional guanosine in the leukemia cDNA, in the 3' untranslated region (the protein sequence is not affected by this difference).

3. Expression of the gene: Expression of the preproTRH gene in normal, leukemia and solid tumor tissues was tested by RT-PCR, as detailed in the protocol herein.

a. expression in normal tissues: A positive signal was found in a fetal brain sample. Absence of PCR amplification was found in the following samples: adult brain, colon, liver, ovary, skin, placenta, lung, kidney, testis, endometrium, bladder, normal peripheral blood leukocytes, normal bone marrow. These results are similar to the expression pattern found in the literature, where the preproTRH gene is found expressed in hypothalamus and other parts of the central nervous system.

b. expression in solid tumors: The following tumor tissues were tested, and were found to be negative for the expression of the preproTRH gene: malignant melanoma, breast cancer, laryngeal carcinoma, lung NSCLC, bladder carcinoma, stomach cancer, lung SCLC, testicle tumor, uterine carcinoma, renal carcinoma, colon carcinoma, tongue cancer, esophageal cancer, ovarian cancer, sarcoma, skin carcinoma. Note that immunoreactive TRH has been detected in human tumors, derived from the neural crest (Wilber, J. F., Clin. Endocr. 59: 3, 1984).

c. Expression in malignant hemopathies: the summary acute myeloid leukemias: 11 positive samples (49 tested)

chronic myeloid leukemias: no positive sample (5 tested)

acute lymphoid leukemias: 4 positive samples (15 tested)

chronic lymphoid leukemias: no positive sample (2 tested)

multiple myeloma: no positive sample (1 tested)

Thus, the expression of the preproTRH gene is found in 23% of acute leukemia samples.

The results can also be presented in relation with the most frequent chromosomal abnormalities found in the acute leukemias:

t(9;22)(q34;q11): 1 positive sample (3 tested)

t(8;21)(q22;q22): 11 positive samples (12 tested)

t(3;21)(q26;q22): 1 positive sample (2 tested)

t(12;21)(p13;q22): 2 positive samples (2 tested)

Inv(16)(p13;q22): 2 positive samples (8 tested)

t(15;17)(q22;q21): no positive samples (4 tested)

11q23 rearrangement: no positive samples (3 tested)

trisomy 8: no positive samples (4 tested)

del 5/5q or del 7/7q: 3 positive samples (8 tested)

There is a clear correlation between the preproTRH gene expression and the acute leukemias with rearrangement of the AML1 gene, located on 21q22, and encoding the AMLcl transcription factor.

4. Conclusion: The preproTRH gene is expressed in human acute leukemia cells. This is a new concept. The expression of the gene is related to chromosomal rearrangements involving the AML1 gene, which are involved in leukemogenesis.

This gene is expressed in normal tissues located in the central nervous system. However, the preproTRH protein is processed through specialized enzymatic pathways in neuron hypothalamic cells to produce the modified tripeptide neurohormone TRH. PreproTRH may be processed differently in leukemic cells. It could accumulate in cell compartments where peptides are efficiently processed and presented to HLA class I molecules. In this case, leukemic cells would carry strong antigenic peptides, while neurons would not. Moreover, cells from the CNS are protected against the cell-mediated immunune system.

The preproTRH gene is expressed in leukemic cells, but not in normal bone marrow, nor in normal PBL. Therefore, its specific and sensitive detection by RT-PCR or other methods is potentially useful as a leukemia-specific tumor marker, for the detection of minimal residual disease, or for the quantitative evaluation of response to treatment after induction chemotherapy.

Example 3

Tryptase-L

1. Cloning the cDNA: The cDNA library NVB329 was prepared as detailed in Example 2 above. The B fraction of the NVB329 cDNA library was screened for tryptase-L clones by hybridizing 40,000 colonies with a $^{33}$P-labelled oligonucleotide probe derived from the sequence of the amplified fragment SIAX DP2-04. Three colonies were found to be positive, and each contained a plasmid (NVB352/1, 2, 3) with a ±2.2–2.5 kb insert oriented in the right direction.

Figure 2:
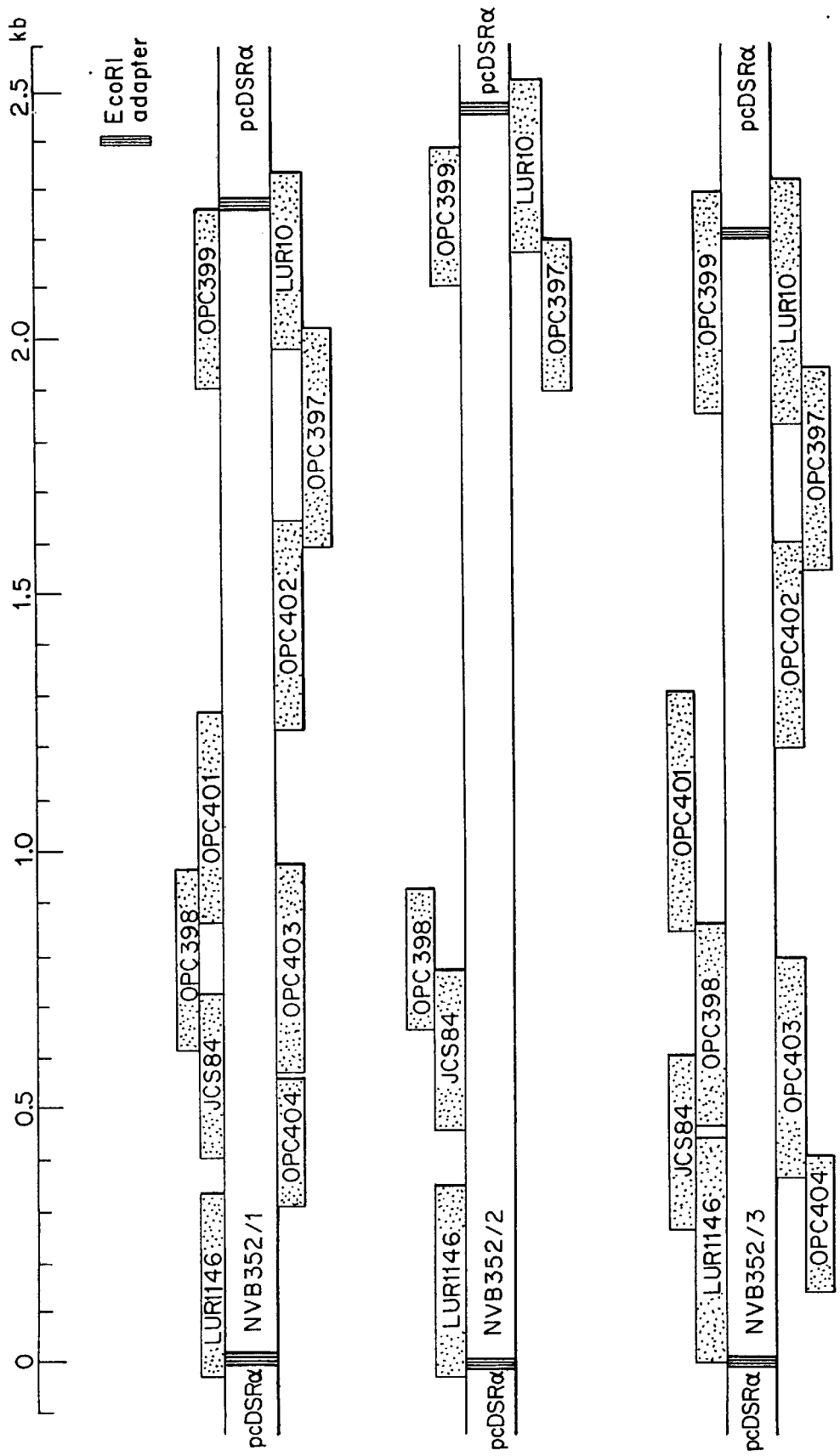
FIG. 2 is a schematic drawing which depicts the sequencing of tryptase-L clones.
Figure 3:
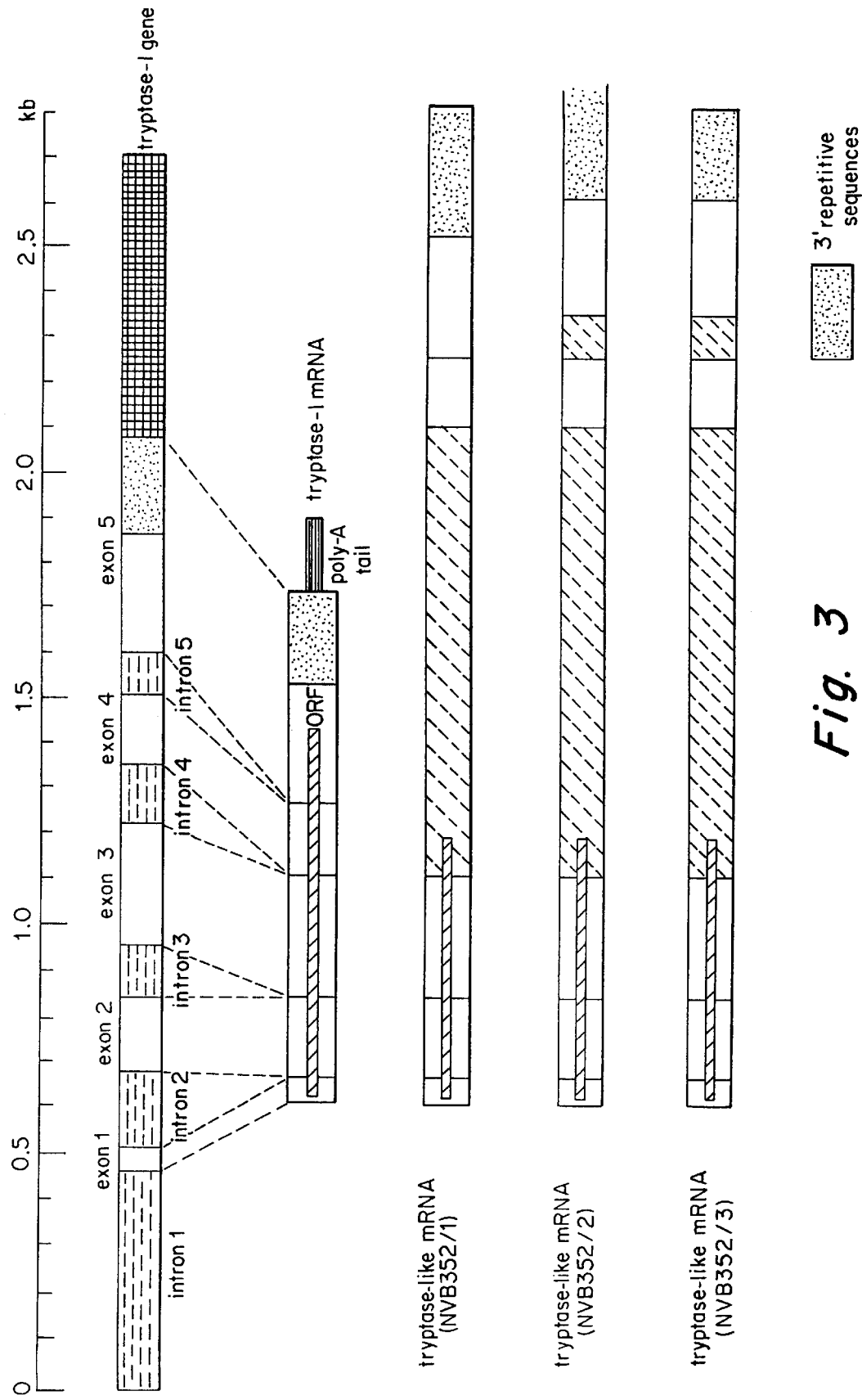
FIG. 3 is a schematic drawing which depicts the relation of tryptase-L clones to the tryptase I gene.

2. Sequencing: Two of the three independent inserts NVB352/1 and NVB352/3 have been sequenced and the partial sequence of clone NVB352/2 has been determined (NVB352/1=SEQ ID NO:3; NVB352/3=SEQ ID NO:5; see FIGS. 2 and 3), using the Delta-Taq Sequencing Kit (Amersham). The three cDNAs come from the same primary RNA transcript, whose sequence has a strong homology with the sequence of the five published tryptase mRNAs (tryptases alpha, beta, I, II, III). The three cDNA clones contain one or two segments that are not present in the tryptase mRNA sequence, and that contain consensus nucleotides similar to those found in the beginning and at the end of introns. The genomic DNAs of the five known tryptase genes contain introns at the same locations. Therefore, we consider that these additional sequences in the 3 cDNA clones are unspliced introns. The deduced protein sequence, if we exclude the unspliced intron sequences, is very similar to the tryptase proteins, and the consensus amino acids for the serine protease activity are conserved. Note that the protein sequence is modified by the unspliced introns in the mRNA.

3. Expression of the gene: Expression of the tryptase-L gene in normal, leukemia and solid tumor tissues was tested by RT-PCR, as detailed in the protocol herewith.

a. Expression in normal tissues: No positive signal was found in the following normal tissue samples: fetal and adult brain, colon, liver, ovary, skin, placenta, lung, kidney, testis, endometrium, bladder, normal peripheral blood leukocytes, normal bone marrow. Note that tryptases are genes specifically expressed in mastocytes. We have not yet tested tryptase-L expression in normal mastocytes by RT-PCR.

b. Expression in solid tumors: The following tumor tissues were tested, and were found to be negative for the expression of the tryptase-L gene: malignant melanoma, breast cancer, laryngeal carcinoma, lung NSCLC, bladder carcinoma, stomach cancer, lung SCLC, testicle tumor, uterine carcinoma, renal carcinoma, colon carcinoma, tongue cancer, esophageal cancer, varian cancer, sarcoma, skin carcinoma.

c. Expression in malignant hemopathies: Thirteen samples have been tested to date (detailed data are enclosed herewith). Six are positive for the expression of tryptase-L, all of them are AMLs. Due to the small sample size, we cannot draw any statistical conclusions, but it is noteworthy that three of the positive samples are AMLs with a t(8;21) translocation.

4. Conclusion: The tryptase-L gene is expressed in human acute myeloid leukemia cells. Its expression has not been found in the normal tissues tested, but it is possible that normal mastocytes express the gene. The expression of the gene is possibly related to the t(8;21) chromosomal rearrangements.

The tryptase-L gene is expressed in leukemic cells, but not in normal bone marrow, nor in normal PBL. Therefore, its specific and sensitive detection by RT-PCR and other methods is useful as a leukemia-specific tumor marker, for the detection of minimal residual disease, or for the quantitative evaluation of response to treatment after induction chemotherapy.

Example 4

SIAX DP2-64/Oct-T1

1. Cloning the eDNA: The cDNA library NVB329 was prepared as detailed in Example 2. The B fraction of the NVB329 cDNA library was screened for SIAX DP2-64 clones by hybridizing 40,000 colonies with a $^{32}$P-labelled PCR probe amplified from SIAX cDNA. One colony was found to be positive (clone CHM329/2-15). The same library was rescreened for SIAX DP2-64 clones by hybridizing 40,000 colonies with a $^{32}$P-labelled PCR probe amplified from SIAX cDNA. 11 colonies were found to be positive (clones CHM363/3, 5, 8).

Figure 5:
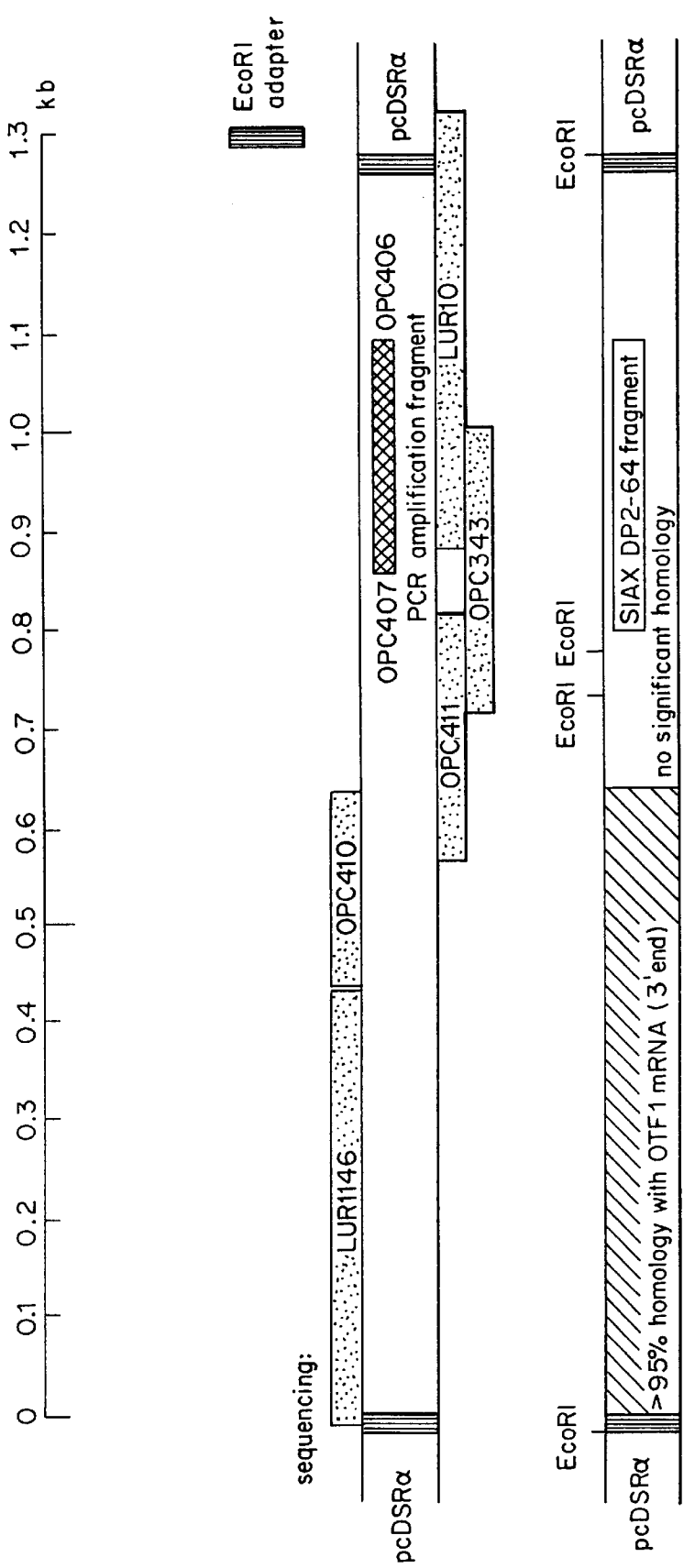
FIG. 5 is a schematic drawing which depicts the CHM 329-2/15 clone of Oct-T1/SIAX DP2-64.
Figure 6:
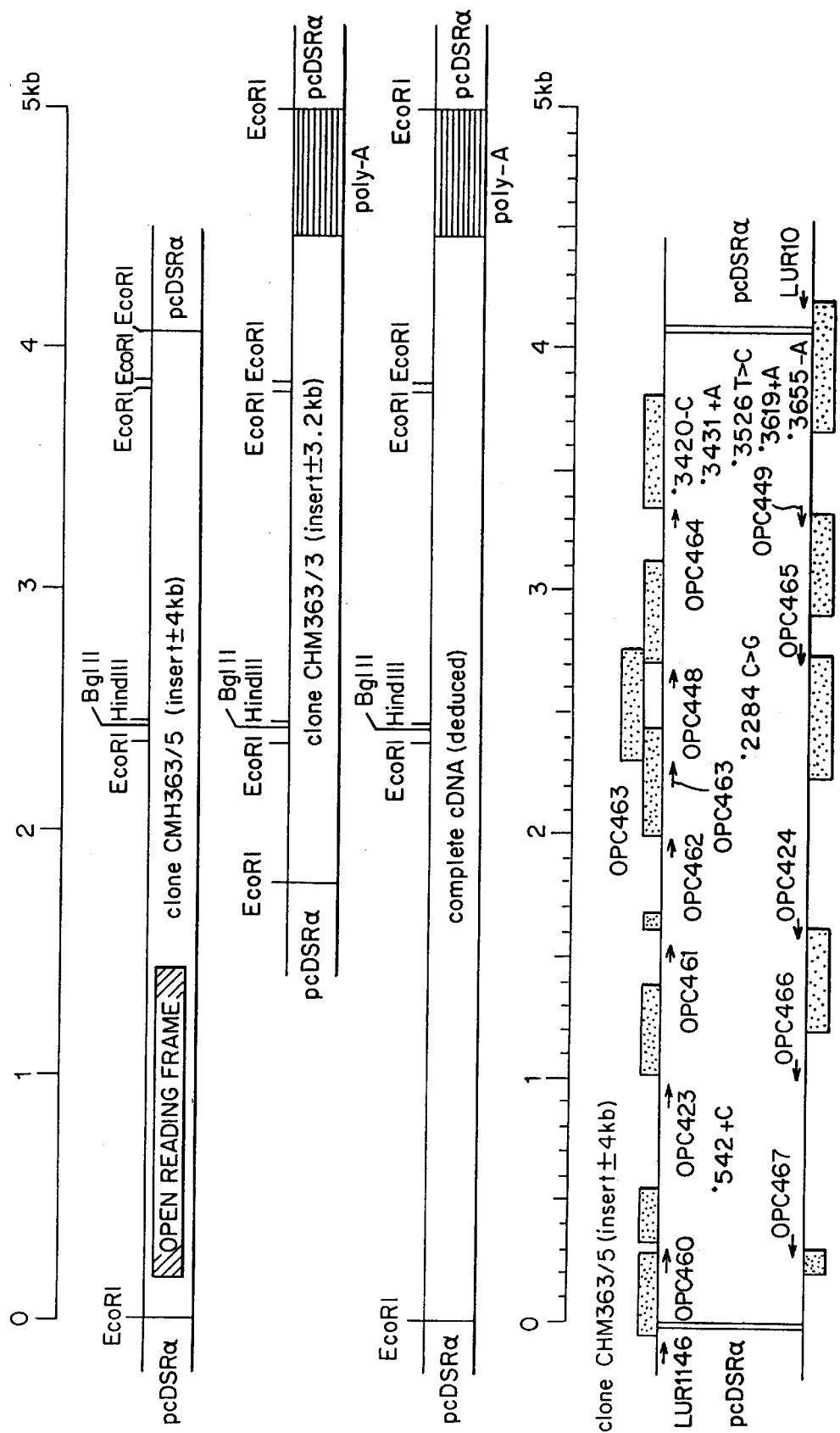
FIG. 6 is a schematic drawing which depicts the sequencing of the CHM363/5 clone of Oct-T1/SIAX DP2-64.

2. Sequencing: Clone CHM329/2-15 has been fully sequenced (SEQ ID NO:7; see FIGS. 4–6), using the Delta-Taq Sequencing Kit (Amersham). Its 3' half has no homology with known genes, while its 5' is completely identical to the 3' end of the Oct-T1 gene, a member of the POU family of transcription factors. (Bhargava A. K. et al., Differential expression of 4 members of the POU family of proteins in activated and PMA-treated Jurkat T cells. *Proc.Natl.Acad..Sci.* 90:10260–10264, November 1993).

Figure 4:
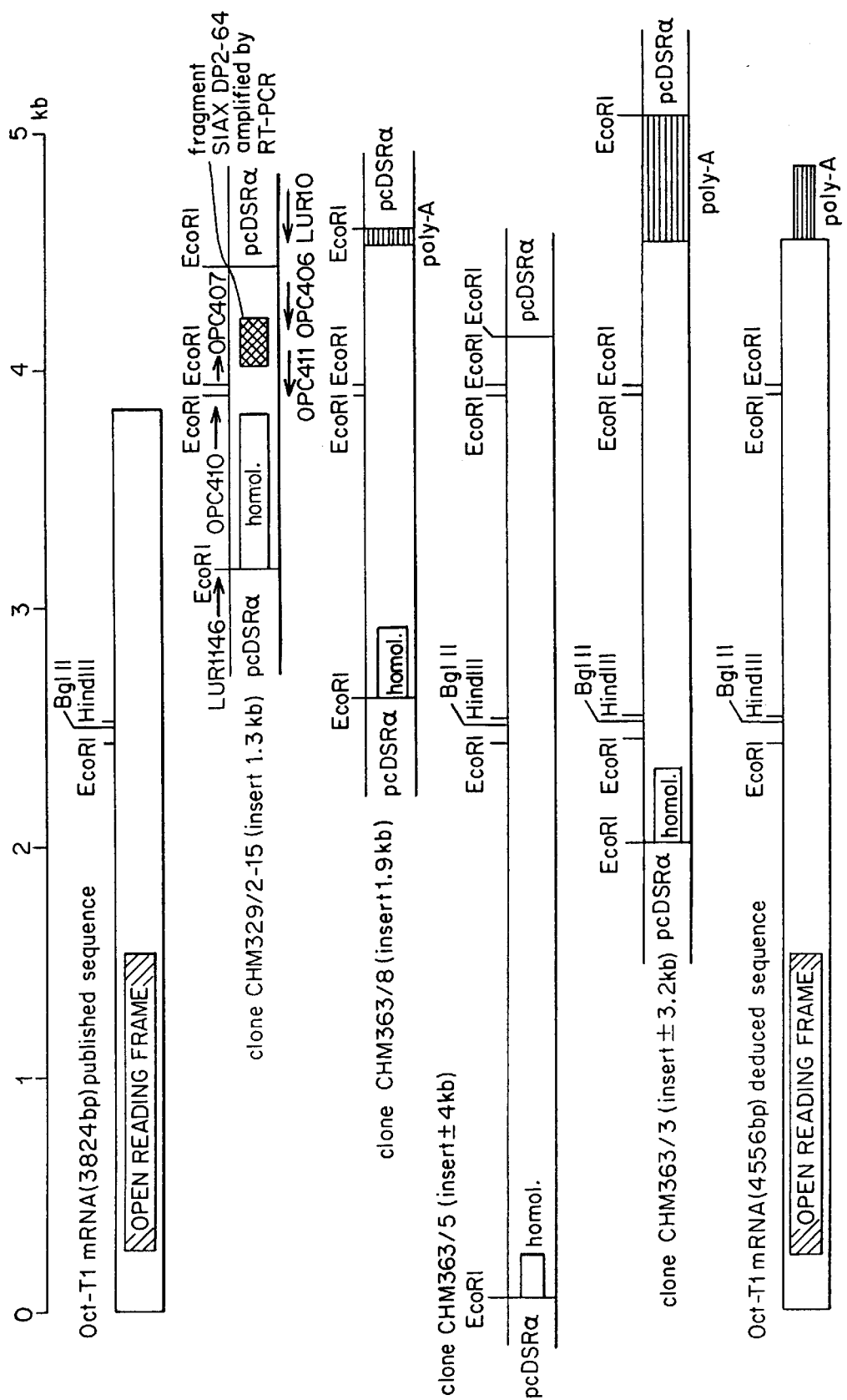
FIG. 4 is a schematic drawing which depicts the Oct-T1/SIAX DP2-64 cDNA clones.

Clones CHM363/3, CHM363/5 and CHM363/8 were sequenced in their 5' extremities, each of which were completely homologous to the Oct-T1 mRNA sequence (see FIG. 4). Clone CHM363/5 has been almost entirely sequenced (see FIG. 5), and is almost completely identical to the Oct-T1 sequence, with minor differences in the 3' untranslated region. Therefore, we can conclude that our SIAX DP2-64 is identical to the previously identified Oct-T1 mRNA. It appears that the published sequence lacks the 3' extremity. We have cloned and sequenced the missing 600 base pairs together with the poly-A tail.

3. Expression of the gene: Expression of the Oct-T1 gene in normal, leukemia and solid tumor tissues was tested by RT-PCR, as detailed in the protocol herewith.

a. Expression in normal tissue: No positive signal was found in the following samples: adult brain, colon, liver, ovary, skin, placenta, lung, kidney, endometrium, bladder, normal peripheral blood leukocytes, normal bone marrow. A positive signal was detected in all the testis samples tested, with the exception of a fetal testis sample.

b. Expression in solid tumors: The following tumor tissues were tested, and were found to be negative for the expression of the Oct-T1 gene: malignant melanoma, breast cancer, laryngeal carcinoma, lung NSCLC, bladder carcinoma, stomach cancer, lung SCLC, testicle tumor, uterine carcinoma, renal carcinoma, colon carcinoma, tongue cancer, esophageal cancer, ovarian cancer, c-skin carcinoma. A positive signal was obtained with an undifferentiated lung sarcoma, but four other sarcoma samples were found to be negative.

c. Expression in malignant hemopathies:

summary:

acute myeloid leukemias: 6 positive samples (49 tested)

chronic myeloid leukemias: no positive samples (5 tested)

acute lymphoid leukemias: 11 positive samples (15 tested)

chronic lymphoid leukemias: no positive samples (2 tested)

multiple myeloma: no positive sample (1 tested)

Thus, the expression of the Oct-T1 gene is found in 11% of acute myeloid leukemia and 73% of acute lymphoid leukemia samples.

The results can also be presented in relation with the most frequent chromosomal abnormalities found in the acute leukemias:

t(9;22)(q34;q11): 1 positive sample (3 tested)

t(8;21)(q22;q22): 10 positive samples (11 tested)

t(3;21)(q26;q22): no positive samples (2 tested)

t(12;21)(p13;q22): 2 positive samples (2 tested)

Inv(16)(p13;q22): no positive samples (8 tested)

t(15;17)(q22;q21): no positive samples (4 tested)

11q23 rearrangement: no positive samples (3 tested)

trisomy 8: no positive samples (4 tested)

del 5/5q or del 7/7q: 3 positive samples (8 tested)

There is a clear correlation between the Oct-T1 gene expression and the acute leukemia with rearrangement of the AML1 gene, located on 21q22, and encoding the AML1 transcription factor.

4. Conclusion: The Oct-T1 gene is expressed in human acute leukemia cells. The gene is particularly frequently expressed in ALL. The expression of the gene is related to chromosomal rearrangements involving the AML1 gene, which are involved in leukemogenesis.

Therefore, it may be possible to immunize leukemia patients against antigens derived from the Oct-T1 protein in the form of peptides presented by HLA class I molecules, and present at the surface of leukemia cells expressing the gene. These antigens should not be present on testis germinal cells, since these do not express HLA class I molecules.

The Oct-T1 gene is expressed in leukemic cells, but not in normal bone marrow, nor in normal PBL. Therefore, its specific and sensitive detection by RT-PCR is potentially useful as a leukemia-specific tumor marker, for the detection of minimal residual disease, or for the quantitative evaluation of response to treatment after induction chemotherapy.

Example 5

RT-PCR assays for the expression of the preproTRH, the tryptase-L, and the Oct-T1/SIAX DP2-64 genes Isolation of total RNA from tumor samples (quickly frozen at −80° C.) was performed by the guanidinium isothiocyanate/cesium chloride procedure (Davis et al., supra). cDNA synthesis was accomplished by extension with oligo(dT)$_{15}$. cDNA was then amplified by PCR with pairs of oligonucleotide primers that are highly specific for each tested gene. To ensure that the RNA was not degraded, a PCR assay with primers specific for β-actin was carried out.

1. cDNA synthesis The concentration of the RNA to be tested was adjusted to in 1 μl of total RNA/3.25 μl of water. The following reagents were mixed in a reaction tube placed in melting ice:

| | |
|---|---|
| Reverse Transcriptase Buffer 5X (Life Technologies Inc., Gaithersburg, MD) | 4 μl |
| dATP 10 mM | 1 μl |
| dCTP 10 mM | 1 μl |
| dGTP 10 mM | 1 μl |
| dTTP 10 mM | 1 μl |
| Dithiothreitol 100 mM | 2 μl |
| oligo(dT)$_{15}$ 20 μM | 2 μl |
| Rnasin 40 units/μl (Promega Corp.) | 0.5 μl |
| M-MLV reverse transcriptase 200 units/μl (Life Technologies, Inc.) | 1 μl |
| Add 2 μg of template RNA | 6.5 μl |
| Total volume: | 20 μl |

The reaction components were mixed and incubated at 42° C. for 60 min. The mixture was then chilled on ice. Water was added (80 μl) to obtain a final volume of 100 μl. The mixture was store at −20° C. until used in PCR.

2. PCR amplification a. Primers preproTRH: sense primer (SEQ ID NO: 7): OPC376: 5'-CCAGCGGCTGCAAGGGGACCA-3'
antisense primer (SEQ ID NO: 8): OPC377: 5'-TGCCCGCCGACCAGGGTGCT-3'
tryptase-L: sense primer (SEQ ID NO: 9): OPC314: 5'-CCCAAGAAGCCCTGAGC-3'
antisense primer (SEQ ID NO: 10): OPC315: 5'-CAAGAAAGGGGAGGGGG-3'
Oct-T1: sense primer (SEQ ID NO: 11): OPC406: 5'-CTGATCTAGTCCCAAGTCACC-3'
antisense primer (SEQ ID NO: 12): OPC407: 5'-ACAGCACTTGATCCAGAGTGG-3'
β-actin sense primer (SEQ ID NO: 13): OPC236: 5'-GGCATCGTGATGGACTCCG-3'
antisense primer (SEQ ID NO: 14): OPC237: 5'-GCTGGAAGGTGGACAGCGA-3' b. PCR reaction: The following reagents were mixed in a reaction tube placed in melting ice:

H$_2$O: 18.5 μl

PCR buffer 10× (Dynazyme): 2.5 μl dNTP (10 mM each): 0.25 μl sense primer (20 μM): 0.5 μl antisense primer (20 μM): 0.5 μl Dynazyme: 0.25 μl cDNA was added (2.5 μl corresponding to 50 ng of total RNA), and the reaction mixture mixed. One drop of mineral oil (Sigma M-3516) was layered on top of the PCR solution. The reaction tube was transferred to the thermocycler for amplification. Positive control: cDNA from SIAX/LB-1079; Negative control: water.

Thermal cycles: The PCR reactions were cycled as follows:

| | |
|---|---|
| First denaturation: | 94° for 5 min |
| Denaturation: | 94° for 1 min |
| Annealing: | |
| preproTRH | 72° for 1 min 28 cycles for amplification of preproTRH gene |
| tryptase-L | 59° for 2 min 35 cycles for amplification of tryptase-L gene |
| Oct-T1 | 63° for 2 min 27 cycles for amplification of Oct-T1 gene |
| β-actin | 68° for 2 min 23 cycles for amplification of β-actin gene |
| Extension: | 72° for 3 min |
| Final extension: | 72° for 15 min |

The reactions were stored at 4° C. until used in agarose gel electrophoresis.

3. Gel electrophoresis Aliquots (10 μl) of the PCR reaction were electrophoresed on a 1% agarose gel stained with ethidium bromide.

TABLE 1

GENE EXPRESSION IN MALIGNANT HEMOPATHIES

| Code | Diagnosis | Karyotype | TRH | OCT-T1 | Tryp-L |
|---|---|---|---|---|---|
| CHIL | AML-M0 | none | – | – | |
| DRIA | AML-M0 | 46, XX, t(4;11)(q21;q23) | +/– | – | – |
| DUMA | AML-M0 | 46, XY | + | + | |
| UMON | AML-M0 | 45, XX, t(9;22), –7 | + | +++ | |
| CABU | AML-M1 | 47, XY, t(9;11)(p22;q23), +21 | – | – | + |
| DEVA | AML-M1 | 46, XX | – | +/– | |
| ELCA | AML-M1 | 46, XY, t(8;21)(q22;q22) | ++ | +++ | + |
| ETIT | AML-M1 | 46, XX, t(4;1;18)(q27;p35;q21), –2, –4, | – | – | |
| GREM | AML-M1 | 46, XX | – | +/– | |
| LENN | AML-M1 | 47, XX, +21 | + | – | |
| MELU | AML-M1 | 46, XX | – | – | |
| KRIM | AML-M1 | 46, XY | – | – | |
| BENA | AML-M1 | 46, XY | – | – | |
| ALVA | AML-M2 | 42, XX, +8 | – | – | – |
| AUWE | AML-M2 | 46, XY, –5, der(7)t(5;7)(q21;q2), +8 | – | – | +++ |
| BOUR | AML-M2 | 45, X, –Y, t(8;17;21)(q22;q11;q22) | ++ | +++ | |
| DUWE | AML-M2 | 47, XY, t(9;22)(q34;q11),(+12), i(17q) | – | – | |
| EVEL | AML-M2 | 46, XX | – | – | – |
| SIAX | AML-M2 | 46, XX, t(8;21)(q22;q22) | +++ | +++ | |
| MARO | AML-M2 | 44, XX, –4, del(5)(q14;q31), –6, –7, | +/– | – | |
| ENIS | AML-M2 | 46, XX, t(8;21)(q22;q22) | ++ | | + |
| RAMA | AML-M2 | 46, XX | +++ | +++ | |
| LEMO | AML-M3 | 46, XY, t(15;17)(q22;q12) | +/– | – | |
| KARA | AML-M3 | 46, XY, t(15;17)(q22;q12) | +/– | +/– | |
| DEVI | AML-M3 | 46, XY, t(15;17)(q22;q12) | – | – | – |
| COWE | AML-M3 | 46, XX, t(15;17)(q22;q12) | +/– | – | |
| LUSE | AML-M4 | 46, XX | – | – | |
| REIB | AML-M4 | 46, XX | +/– | – | |
| RICO | AML-M4 | 46, XY | – | – | |
| AERT | AML-M4 | 46, XX | – | – | |
| GIHA | AML-M4 | 46, XY | – | – | |
| ERTE | AML-M4Eo | 46, XX, inv(16) | + | – | |
| TEEN | AML-M5 | 46, XY, t(8;11)(p22;q23) | – | – | |
| DOMA | AML-M5 | 46, XX, del(7)(q22) | +++ | – | |
| ROCH | AML-M5a | | – | – | |
| DANA | AML-M5b | 46, XY | – | – | |
| LATT | AML-M5b | 1) 46, XY, –5, ins(12;?)(p12;?), +M | – | – | |
| LIAK | AML-M5b | 1) 46, XX, inv(16) | – | – | + |
| OBBE | AML-M5b | 46, XX | – | – | |
| RYRO | AML-M5b | 46,XX | – | – | |
| LINT | AML-M5b | 46, XY, inv(16) | + | – | |
| RONI | AML-M5b | 46, XX | – | – | |
| TERE | AML-M5b | 47, XY, t(2;7)(p1?4;p22), +8 [10] | – | – | |
| ERNI | AML-M5b | del 1q, trisomie 8 | – | – | |
| LOLI | AML-M5b | 46, XY | – | – | |
| NIES | AML-M6 | 44, XY, del(2)(q12;q14), del(7)(q32), | +/– | – | |
| REUT | AML-M6 | 46, XX | +/– | – | |
| GALU | AML-M6 | 44, XX, t(5;17)(p14;q11), –14, –20 | +/– | – | |
| OLBE | AML-M6 | 46, XX, t(21;21) | – | – | |
| GRAD | CLL | 46, XX | – | – | |
| JEUM | CLL | 46, XY | – | – | |
| DERU | CML | 46, XX, t(9;22)(q34;q11) | – | – | |
| LOUY | CML | 46, XY, t(9;22) | – | – | |
| NEIR | CML | 46, XY, t(9;22)(q34;q11) | – | – | |
| VIER | CML | 46, XY, t(9;22) | – | – | – |
| CAVA | ALL | 1) 47, XY, t(9;22)(q34;q11), –9, | – | ++ | |
| AGUI | common ALL | 1)47,XY,t(9;22)(q34;q11),–9 | – | ++ | |
| DRON | common ALL | 46, XX | +/– | – | |
| GERN | common ALL | 45, XY, –7, t(7;16)(q11.2;q24), –18, +mar | + | + | |

TABLE 1-continued

GENE EXPRESSION IN MALIGNANT HEMOPATHIES

| Code | Diagnosis | Karyotype | TRH | OCT-T1 | Tryp-L |
|------|-----------|-----------|-----|--------|--------|
| ISER | common ALL | 46, XX, −7, del(12)(p11.?2), +mar | − | + | |
| LULL | common ALL | 47, X, der(X), del(1)(q25;q42), −3, t(6;22) | +/− | ++ | |
| MEUL | common ALL | 47,XX,−2,der(2)t(2;9)(?p16;p23),del(12)(p13) | − | ++ | |
| SACK | common ALL | not known | − | − | |
| WIRA | common ALL | 46, XY | + | + | |
| DANN | common ALL | 46, XX | ++ | + | − |
| POEL | common ALL | 46, XY | + | ++ | |
| FURM | common ALL | 46, XY, −18, +mar | +/− | ++ | |
| AMAY | common ALL | | − | − | |
| QUEL | MM | 81,XX,?add(5)(q3?2),−8,−9,−12,+15,−16,+22, | 31 | − | |
| ORBA | MM | | | | |
| BETT | T-ALL | 46, XY, del (7)(p13) | +/− | + | − |
| JASI | T-ALL | 46, XX | − | + | |
| OUSA | T-ALL | 47, XY, +7 | − | − | |

N.B. results are expressed as relative intensity on the agarose gel, as compared with positive control (SIAX), arbitrarily assigned +++ (+, ++, +++ results are considered positive; −, +/− results are considered negative).

Example 6
Identification of the portion of leukemia associated genes encoding a tumor rejection antigens.

In a first method, available CTL clones directed against antigens presented by autologous tumor cells shown to express one or more of the leukemia associated genes are screened for specificity against COS cells transfected with preproTRH, tryptase-L and/or Oct-T1 genes and autologous HLA alleles as described by Brichard et al. (*Eur. J. Immunol.* 26:224–230, 1996). CTL recognition of preproTRH, tryptase-L and/or Oct-T1 is determined by measuring release of TNF from the cytolytic T lymphocyte or by $^{51}$Cr release assay (Herin et al., *Int. J. Cancer* 39:390–396, 1987). If a CTL clone specifically recognizes a transfected COS cell, shorter fragments of the coding sequences are prepared and tested by transfecting COS cells to identify the region of the gene that encodes the peptide recognized by the CTL. Fragments of preproTRH, tryptase-L and/or Oct-T1 are prepared by exonuclease III digestion or other standard molecular biology methods such as PCR. Synthetic peptides are prepared and tested to confirm the exact sequence of the antigen.

Alternatively, CTL clones are generated by stimulating the peripheral blood lymphocytes (PBLs) of a patient with autologous normal cells transfected with DNA clones encoding preproTRH, tryptase-L and/or Oct-T1 polypeptides (e.g. SEQ ID NOs:1, 3, 5 and/or 7) or with irradiated PBLs loaded with synthetic peptides corresponding to the putative proteins and matching the consensus for the appropriate HLA class I molecule to localize the antigenic peptide within the preproTRH, tryptase-L and/or Oct-T1 clones (see, e.g., van der Bruggen et al., *Eur. J. Immunol.* 24:3038–3043, 1994; MAGE3 peptides presented by HLA.A2). The HLA type of the patient from which the leukemia cells from which preproTRH, tryptase-L and Oct-T1 were isolated is: A2, A26, B7, B56, Cw1, DR1, DR8, DQ4, DQ5.

Optionally, shorter fragments of preproTRH, tryptase-L and/or Oct-T1 cDNAs are generated by PCR. Shorter fragments are used to provoke TNF release or $^{51}$Cr release as above.

Example 7
Identification of leukemia associated gene encoded tumor rejection antigen peptides Synthetic peptides corresponding to portions of the shortest fragment of preproTRH, tryptase-L and/or Oct-T1 which provokes TNF release are prepared. Progressively shorter peptides are synthesized to determine the optimal preproTRH, tryptase-L and/or Oct-T1 tumor rejection antigen peptides for a given HLA molecule.

Synthetic peptides are tested for lysis of HLA expressing cells according to known procedures. For example, if the HLA which presents a peptide of interest is determined to be HLA-A2, then T2 cells can be used. T2 cells are HLA-A2$^+$ cells which have an antigen-processing defect resulting in an increased capacity to present exogenous peptides. T2 cells are mixed with a synthetic peptide corresponding to the CTL-reactive portion of preproTRH, tryptase-L or Oct-T1. CTL cells are added and lysis is measured after 4 hours to determine which peptides efficiently stimulate the lysis of T2 cells bearing HLA-A2. Other HLA expressing cells are known in the art or can be prepared by transfection with specific HLA clones.

To determine the optimal size of the synthetic peptide, peptides of decreasing size are synthesized based on the sequence of the peptide deterined above, by successively removing one amino acid from the amino terminal end or the carboxy terminal end of the peptide. These peptides are tested for the ability to induce cell lysis of appropriate HLA expressing cells by CTL cells in a dose response assay. Lyophilized peptides are dissolved at 20 mg/ml in DMSO, then diluted to 2 mg/ml in 10 mM acetic acid and stored at −80° C. Target cells, e.g. HLA-A2$^+$ T2 cells, are labeled with $^{51}$Cr, as described above, for 1 hour at 37° C. followed by extensive washing to remove unincorporated label. To confirm the necessity of the interaction of the peptide with the HLA, T2 cells optionally can be pretreated with an anti-HLA-A2 antibody, such as MA2.1 (Wölfel et al., *Eur. J. Immunol.* 24: 759–764, 1994), and then are incubated in 96-well microplates in the presence of various concentrations of peptides for 30 minutes at 37° C. CTLs which recognize the peptide presented by the HLA are then added in an equal volume of medium at an effector:target ratio of 30:1. Chromium-51 release is measured after 4 hours.

Example 8
Determination of the recognition of homologous peptides of genes related to leukemia associated genes by CTLs As noted above, Oct-T1 and tryptase-L have high amino acid homology to other Oct family transcription factors and other tryptases. To demonstrate that a tumor rejection antigen derived from Oct-T1 and/or tryptase-L is specific for these genes, peptides of other Oct and tryptase proteins which correspond to the postitions in the respective proteins of Oct-T1 and tyrptase-L are synthesized and used in a dose response-chromium release assay as described above. This experiment permits the determination of the specificity of the Oct-T1 and/or tryptase-L derived TRAs, such that TRAs which selectively provoke lysis of cells which express Oct-T1 and/or tryptase-L, but not homologous genes, can be selected.

Example 9

Normal cells are not lysed by CTLs which lyse cells which express leukemia associated genes This example describes CTL lysis experiments with various cell lines with or without incubation with the leukemia associated gene derived peptides determined above. SIAX leukemic cells, normal B cells from patient SIAX transformed with EBV (SIAX-EBV) and normal peripheral blood lymphocytes from the same patient (SIAX-PBL) are tested for lysis by CTL cells in a dose response assay. These cells are incubated with CTLs at the effector/target ratios determined to be optimal in the dose response assays detailed above, and assayed for lysis as described above. Lysis of only the SIAX leukemic cells by the CTLs, demonstrates that SIAX-EBV and SIAX-PBL cells are not recognized by the CTLs because such cells do not normally express the tumor rejection antigen derived from preproTRH, tryptase-L and/or Oct-T1 proteins.

It is next determined whether these cells would be lysed by CTL if pulsed with a peptide derived from preproTRH, tryptase-L and/or Oct-T1. The peptides selected on the basis of the experiments above are tested for the ability to induce cell lysis of SIAX leukemic cells, SIAX-EBV cells, and non-autologous cells which express the appropriate HLA by CTL cells in a dose response assay as in previous examples. SIAX-EBV and SIAX-PBL pulsed with preferred peptides are not lysed by CTLs, but SIAX leukemic cells and the non-autologous cells pulsed with preferred peptides are lysed by CTLs.

Other aspects of the invention will be clear to the skilled artisan and need not be repeated here.

The terms and expressions which have been employed are used as terms of description and not of limitation, and there is no intention in the use of such terms and expressions of excluding any equivalents of the features shown and described or portions thereof, it being recognized that various modifications are possible within the scope of the invention.

A sequence listing is presented followed by what is claimed:

We claim:

1. A method for diagnosing a disorder characterized by expression of a leukemia associated nucleic acid molecule, comprising:

contacting a biological sample isolated from a subject with an agent that is specific for the leukemia associated nucleic acid molecule, wherein the leukemia associated nucleic acid molecule hybridizes under stringent conditions to a molecule having a nucleotide sequence selected from the group consisting of SEQ ID NO:1, SEQ ID NO:3, SEQ ID NO:5 and SEQ ID NO:7, and determining the interaction between the agent and the leukemia associated nucleic acid molecule as a determination of the disorder.

2. The method of claim 1 wherein the agent is a nucleic acid molecule comprising a molecule having a nucleotide sequence selected from the group consisting of SEQ ID NO:1, SEQ ID NO:3, SEQ ID NO:5, SEQ ID NO:7, fragments thereof, and complements thereof.

3. The method of claim 1, wherein the agent comprises a nucleic acid molecule having the nucleotide sequence of SEQ ID NO:1 or a fragment thereof.

4. The method of claim 3, wherein the biological sample is isolated from a non-fetal-brain tissue.

5. The method of claim 1, wherein the agent comprises a nucleic acid molecule having the nucleotide sequence of SEQ ID NO:3 or SEQ ID NO:5 or a fragment thereof.

6. The method of claim 5, wherein the biological sample is isolated from a non-mastocyte tissue.

7. The method of claim 1, wherein the agent comprises a nucleic acid molecule having the nucleotide sequence of SEQ ID NO:7 or a fragment thereof.

8. The method of claim 7, wherein the biological sample is isolated from a non-fetal-testis tissue.

9. The method of claim 1 wherein the interaction is determined by amplifying at least a portion of the nucleic acid molecule.

* * * * *